(12) United States Patent
Silver et al.

(10) Patent No.: US 10,517,839 B2
(45) Date of Patent: Dec. 31, 2019

(54) MAST CELL INHIBITION IN DISEASES OF THE RETINA AND VITREOUS

(75) Inventors: Randi B. Silver, New York, NY (US); Nathan O'Connor, New York, NY (US)

(73) Assignee: Cornell University, Ithaca, NY (US)

( * ) Notice: Subject to any disclaimer, the term of this patent is extended or adjusted under 35 U.S.C. 154(b) by 194 days.

(21) Appl. No.: 12/455,958

(22) Filed: Jun. 9, 2009

(65) Prior Publication Data

US 2009/0318545 A1    Dec. 24, 2009

Related U.S. Application Data

(60) Provisional application No. 61/060,029, filed on Jun. 9, 2008.

(51) Int. Cl.
*A61K 31/352* (2006.01)
*A61P 27/02* (2006.01)
*A61K 31/136* (2006.01)
*A61K 31/4741* (2006.01)

(52) U.S. Cl.
CPC .......... *A61K 31/136* (2013.01); *A61K 31/352* (2013.01); *A61K 31/4741* (2013.01)

(58) Field of Classification Search
CPC . A61K 31/136; A61K 31/352; A61K 31/4741
See application file for complete search history.

(56) References Cited

U.S. PATENT DOCUMENTS

| | | | |
|---|---|---|---|
| 3,561,444 A | 2/1971 | Boucher | |
| 3,703,173 A | 11/1972 | Dixon | |
| 4,051,842 A | 10/1977 | Hazel et al. | |
| 4,140,122 A | 2/1979 | Kuhl et al. | |
| 4,383,529 A | 5/1983 | Webster | |
| 4,617,407 A | 10/1986 | Young et al. | |
| 4,624,251 A | 11/1986 | Miller | |
| 4,635,627 A | 1/1987 | Gam et al. | |
| 4,703,038 A | 10/1987 | Garthoff et al. | |
| 4,871,865 A | 10/1989 | Lever, Jr. et al. | |
| 4,898,732 A | 2/1990 | Fernandez | |
| 4,923,875 A | 5/1990 | Frost | |
| 4,962,091 A | 10/1990 | Eppstein et al. | |
| 5,019,591 A | 5/1991 | Gardner et al. | |
| 5,030,623 A | 7/1991 | Gruber | |
| 5,114,937 A | 5/1992 | Hamby | |
| 5,145,859 A | 9/1992 | Fleischmann | |
| 5,192,780 A | 3/1993 | York et al. | |
| 5,250,529 A | 10/1993 | Theoharides | |
| 5,624,962 A * | 4/1997 | Takeuchi et al. | 514/772.2 |
| 5,641,673 A | 6/1997 | Haseloff et al. | |
| 5,641,805 A | 6/1997 | Hayakawa et al. | |
| 5,643,899 A | 7/1997 | Elias et al. | |
| 5,693,619 A | 12/1997 | LaVallee et al. | |
| 5,869,079 A | 2/1999 | Wong et al. | |
| 5,994,357 A | 11/1999 | Theoharides | |
| 6,008,003 A | 12/1999 | Haak-Frendscho et al. | |
| 6,153,187 A | 11/2000 | Yacoby-Zeevi | |
| 6,207,684 B1 | 3/2001 | Aberg | |
| 6,221,914 B1 | 4/2001 | Burgess et al. | |
| 6,225,327 B1 * | 5/2001 | Miller | A61K 9/0048 514/342 |
| 6,225,356 B1 | 5/2001 | Jones, III | |
| 6,297,399 B1 | 10/2001 | Walsh et al. | |
| 6,316,258 B1 | 11/2001 | Noble et al. | |
| 6,335,327 B1 | 1/2002 | Ogawa et al. | |
| 6,362,216 B1 | 3/2002 | Burgess et al. | |
| 6,372,724 B1 | 4/2002 | Pelleg et al. | |
| 6,423,705 B1 | 7/2002 | Tracey et al. | |
| 6,433,018 B1 | 8/2002 | Siddiqui et al. | |
| 6,518,277 B1 | 2/2003 | Sadhu et al. | |
| 6,559,168 B2 | 5/2003 | Marfat et al. | |
| 6,635,625 B2 | 10/2003 | Theoharides | |
| 6,673,802 B2 | 1/2004 | Castelhano et al. | |
| 6,689,748 B1 | 2/2004 | Theoharides | |
| 6,825,219 B2 | 11/2004 | Cywin et al. | |
| 7,071,183 B2 | 7/2006 | Montgomery et al. | |
| 7,115,266 B2 | 10/2006 | Bachmann | |
| 7,115,777 B2 | 10/2006 | Allmendinger | |
| 2001/0046474 A1 | 11/2001 | Weers et al. | |
| 2003/0007992 A1 | 1/2003 | Gibson et al. | |
| 2004/0097486 A1 | 5/2004 | Yanni | |

(Continued)

FOREIGN PATENT DOCUMENTS

| | | |
|---|---|---|
| CA | 2227112 | 7/1998 |
| CA | 2245776 | 2/1999 |
| DE | 3112262 A1 | 2/1982 |
| DE | 3741414 A1 | 6/1989 |
| EP | 0321201 A2 | 6/1989 |
| EP | 0918515 B1 | 6/1999 |
| WO | WO-94/07529 A1 | 4/1994 |
| WO | WO-99/13874 A1 | 3/1999 |
| WO | WO-9943663 A1 | 9/1999 |
| WO | WO-00/64873 A1 | 11/2000 |
| WO | WO-02/28366 A2 | 4/2002 |
| WO | WO-02/089884 A1 | 11/2002 |
| WO | WO-03/000694 A1 | 1/2003 |
| WO | WO-03/008004 A1 | 1/2003 |
| WO | WO-03/053366 A2 | 7/2003 |
| WO | WO-2005/037317 A2 | 4/2005 |

OTHER PUBLICATIONS

Quam et al., (Investigative Ophthalmology & Visual Science, Sep. 2001, vol. 42, 2408-2413).*

(Continued)

*Primary Examiner* — Zohreh A Fay
(74) *Attorney, Agent, or Firm* — Schwegman, Lundberg & Woessner, P.A.

(57) ABSTRACT

This application discloses methods for treating or preventing an ophthalmic retinal vascular permeability, angiogenic or fibroproliferative disease, disorder or condition that involve administering to a patient in need thereof a composition that can inhibit mast cell migration into the vitreous or the retina, mast cell proliferation in the vitreous or the retina, or mast cell secretion into the vitreous or the retina.

6 Claims, 18 Drawing Sheets

(8 of 18 Drawing Sheet(s) Filed in Color)

Specification includes a Sequence Listing.

(56) References Cited

U.S. PATENT DOCUMENTS

| | | |
|---|---|---|
| 2004/0259952 A1 | 12/2004 | Abbas et al. |
| 2005/0209141 A1 | 9/2005 | Silver et al. |
| 2005/0261641 A1 | 11/2005 | Warchol et al. |
| 2006/0110428 A1* | 5/2006 | deJuan et al. ............... 424/427 |
| 2006/0177483 A1* | 8/2006 | Byrne et al. ................. 424/427 |
| 2008/0032918 A1 | 2/2008 | Silver et al. |
| 2009/0009351 A1 | 1/2009 | Lamontagne |
| 2009/0081274 A1 | 3/2009 | Silver et al. |

OTHER PUBLICATIONS

"U.S. Appl. No. 10/964,567, Final Office Action dated Oct. 24, 2006", 18 pgs.
"U.S. Appl. No. 10/964,567, Non Final Office Action dated Mar. 30, 2006", 14 pgs.
"U.S. Appl. No. 10/964,567, Preliminary Amendment dated Jan. 31, 2005", 3 pgs.
"U.S. Appl. No. 10/964,567, Response filed Feb. 3, 2006 to Restriction Requirement dated Dec. 6, 2005", 11 pgs.
"U.S. Appl. No. 10/964,567, Response filed Jun. 28, 2006 to Non Final Office Action dated Mar. 30, 2006", 17 pgs.
"U.S. Appl. No. 10/964,567, Restrication Requirement dated Dec. 6, 2005", 8 pgs.
"U.S. Appl. No. 11/657,343, Examiner Interview Summary dated Nov. 28, 2008", 2 pgs.
"U.S. Appl. No. 11/657,343, Non-Final Office Action dated Mar. 25, 2008", 11 pgs.
"U.S. Appl. No. 11/657,343, Preliminary Amendment dated Aug. 16, 2007", 7 pgs.
"U.S. Appl. No. 11/657,343, Response filed Jan. 25, 2008 to Restriction Requirement dated Dec. 26, 2007", 8 pgs.
"U.S. Appl. No. 11/657,343, Restriction Requirement dated Dec. 26, 2007", 10 pgs.
"U.S. Appl. No. 12/237,176, Examiner Interview Summary dated Sep. 7, 2010", 3 pgs.
"U.S. Appl. No. 12/237,176, Final Office Action dated Jan. 20, 2011", 12 pgs.
"U.S. Appl. No. 12/237,176, Non-Final Office Action dated Jun. 23, 2010", 12 pgs.
"U.S. Appl. No. 12/237,176, Response filed Mar. 31, 2010 to Restriction Requirement dated Mar. 19, 2010", 8 pgs.
"U.S. Appl. No. 12/237,176, Response filed Oct. 20, 2010 to Non Final Office Action dated Jun. 23, 2010", 15 pgs.
"U.S. Appl. No. 12/237,176, Response filed Dec. 29, 2009 to Restriction Requirement dated Sep. 1, 2009", 6 pgs.
"U.S. Appl. No. 12/237,176, Restriction Requirement dated Mar. 19, 2010", 6 pgs.
"U.S. Appl. No. 12/237,176, Restriction Requirement dated Sep. 1, 2009", 10 pgs.
"Registry Entry for RN 15826-37-6", Cromolyn Sodium, 2 pgs.
Abiko, T., et al., "Synthesis of Six Analogues and Their Two Fragments Related to L-α-Hydroxyisovaleryl-Leu-Val-Phe-OMs as Renin Inhibitor", *Biochemical and Biophysical Research Communications*, 100(1), (May 15, 1981), 177-183.
Airaksinen, K. E. J., "Autonomic Mechanisms and Sudden Death After Abrupt Coronary Occulsion", *Annals of Medicine*, 31, (1999), 240-245.
Akasu, M., et al., "Differences in Tissue Angiotensin II-Forming Pathways by Species and Organs In Vitro", *Hypertension*, 32, (1998), 514-520.
Alexander, S. P. H., et al., "TiPS Nomenclature Supplement 2001", *TRENDS in Pharmacological Sciences—2001 Nomenclature Supplement*, (12th Edition), (2001), 2 pgs.
Aviv, A., "The Links Between Cellular $Ca^{2+}$ and $Na^+ / H^+$ Exchange in the Pathophysiology of Essential Hypertension", *American Journal of Hypertension*, 9, (1996), 703-707.
Bader, M., et al., "Tissue Renin-Angiotensin Systems: New Insights From Experimental Animal Models in Hypertension Research", *Journal of Molecular Medicine*, 79, (2001), 76-102.

Bae, Y.-S., et al., "Identification of a Compound That Directly Stimulates Phospholipase C Activity", *Molecular Pharmacology*, 63(5), (2003), 1043-1050.
Baram, D., et al., "Synaptotagmin II Negatively Regulates $CA^{2+}$-triggered Exocytosis of Lysosomes in Mast Cells", *Journal of Experimental Medicine*, 189(10), (1999), 1649-1658.
Barlucchi, L., et al., "Canine Ventricular Myocytes Possess a Renin-Angiotensin System That is Upregulated With Heart Failure", *Circulation Research*, 88(3), (2001), 298-304.
Becker, B. N., et al., "Renin-Angiotensin System Gene Expression in Post-Transplant Hypertension Predicts Allograft Function", *Transplantation*, 69(7), (2000), 1485-1491.
Beg, Z. H., et al., "Modulation of 3-Hydroxy-3-Methylglutaryl Coenzyme: A Reductase Activity With cAMP and With Protein Fractions of Rat Liver Cytosol", *Biochemical and Biophysical Research Communications*, 54(4), (1973), 1362-1369.
Benech, J. C., et al., "CA2+ Dynamics in Synaptosomes Isolated From the Squid Optic Lobe", *Journal of Neuroscience Research*, 62, (2000), 840-846.
Benedict, C. R., et al., "Prognostic Significance of Plasma Norepinephrine in Patients With Asymptomatic Left Ventricular Dysfunction", *Circulation*, 94(4), (1996), 690-697.
Berridge, M. J., "Inositol Trisphosphate and Calcium Signalling", *Nature*, 361(6410), (Jan. 28, 1993), 315-325.
Berry, C., et al., "Angiotensin Receptors: Signaling, Vascular Pathophysiology, and Interactions With Ceramide", *American Journal of Physiology—Heart, Circulation and Physiology*, 281(6), (2001), H2337-H2365.
Bertrand, B., et al., "The $Na^+/H^+$ Exchanger Isoform 1 (NHE1) Is a Novel Member of the Calmodulin-Binding Proteins", *The Journal of Biological Chemistry*, 269(18), (1994), 13703-13709.
Bian, J.-S., et al., "Phospholipase C Inhibitors Attenuate Arrhythmias Induced by K-Receptor Stimulation in the Isolated Rat Heart", *Journal of Molecular Cell Cardiology*, 30, (1998), 2103-2110.
Bleasdale, J. E., et al., "Selective Inhibition of Receptor-Coupled Phospholipase C-Dependent Processes in Human Platelets and Polymorphonuclear Neutrophils", The *Journal of Pharmacology and Experimental Therapeutics*, 255(2), (1990), 756-768.
Bock, M. G., et al., "Dipeptide Analogues. Synthesis of a Potent Renin Inhibitor", *Journal of the Chemical Society, Chemical Communications* (Issue 3), (1985), 109-110.
Boger, D. H., et al., "Novel Renin Inhibitors Containing the Amino Acid Statine", *Nature*, 303, (1983), 81-82.
Bragat, A. C., et al., "Effect of High-Performance Liquid Chromatography on Plasma Angiotensin II Measurements in Treated and Untreated Normotensive and Hypertensive Patients", *Journal of Hypertension*, 15, (1997), 459-465.
Brasch, H., et al., "Angiotensin II Increases Norepinephrine Release From Atria by Acting on Angiotensin Subtype 1 Receptors", *Hypertension*, 22, (1993), 699-704.
Brooks, A. C., et al., "Reactive Oxygen Species Generation and Histamine Release by Activated Mast Cells: Modulation by Nitric Oxide Synthase Inhibition", *British Journal of Pharmacology*, 128, (1999), 585-590.
Burton, J., et al., "Competitive Inhibitors of Renin. Inhibitors Effective at Physiologiccal pH", *Biochemistry*, 41(17), (1975), 3892-3898.
Campbell, D. J., "Circulating and Tissue Angiotensin Systems", *Journal of Clinical Investigation*, 79, (1987), 1-6.
Campbell, Jr., W. G., et al., "Plasma and Renal Prorenin/Renin, Renin mRNA, and Blood Pressure in Dahl Salt-Sensitive and Salt-Resistant Rats", *Hypertension*, 27, (1996), 1121-1133.
Cardin, S., et al., "Evolution of the Atrial Fibrillation Substrates in Experimental Congestive Heart Failure: Angiotensin-Dependent and -Independent Pathways", *Cardiovascular Research*, 60, (2003), 315-325.
Cech, T. R., "Ribozyme Engineering", *Current Opinion in Structural Biology*, 2(4), (Aug. 1992), 605-609.
Cech, T. R., "Self-Splicing of Group I Introns", *Annual Review of Biochemistry*, 59, (1990), 543-568.
Cech, T. R., "The Chemistry of Self-Splicing RNA and RNA Enzymes", *Science*, 236(4808), (1987), 1532-1539.

(56) References Cited

OTHER PUBLICATIONS

Chen, C.-C., et al., "Protein Kinase C Isoform σ Is Involved in the Stimulation of the Na$^+$-H$^+$ Exchanger in C$_6$ Clioma Cells", *Molecular Pharmacology*, 48(6), (1995), 995-1003.

Cody, R. J., et al., "A Substrate Analog Inhibitor of Renin That is Effective in vivo", *Biochemical and Biophysical Research Communications*, 97(1), (Nov. 17, 1980), 230-235.

Couture, L. A., "Anti-Gene Therapy: The Use of Ribozymes to Inhibit Gene Function", *Trends in Genetics*, 12(12), (1996), 510-515.

Danser, A. H. J., et al., "Prorenin, Renin, Angiotensinogen, and Angiotensin-Converting Enzyme in Normal and Failing Human Hearts", *Circulation*, 96, (1997), 220-226.

Dart, A. M., et al., "Unexpected Drug Effects on Autonomic Function During Myocardial Ischaemia", *Cardiovascular Research*, 27(6), (1993), 906-914.

De Gasparo, M., et al., "International Union of Pharmacology. XXIII. The Angiotensin II Receptors", *Pharmacological Reviews*, 52(3), (2000), 415-472.

De Lannoy, L. M., et al., "Angiotensin Converting Enzyme is the Main Contributor to Angiotensin I-II Conversion in the Interstitium of the Isolated Perfused Rat Heart", *Journal of Hypertension*, 19, (2001), 959-965.

De Mello, W. C., "Cardiac Arrhythmias: The Possible Role of the Renin-Angiotensin System", *Journal of Molecular Medicine*, 79, (2001), 103-108.

Deli'Italia, L. J., et al., "Compartmentalization of Angiotensin II Generation in the Dog Heart", *The Journal of Clinical Investigation*, 100(2), (1997), 253-258.

Demoz, M., et al., "Transforming by Oncogenic Ras-p21 Alters the Processing and Subcellular Localization of the Lysosomal Protease Cathepsin D", *Journal of Cellular Biochemistry*, 73(1), (1999), 370-378.

Dieter, P., "RO 31-8220 and RO 31-7549 Show Improved Selectivity for Protein Kinase C Over Staurosporine in Macrophages", *Biochemical and Biophysical Research Communications*, 181(1), (Nov. 27, 1991), 396-401.

Dinh, D. T., et al., "Angiotensin Receptors: Distribution, Signalling and Function", *Clinical Science*, 100, (2001), 481-492.

Dostal, D. E., et al., "The Cardiac Renin-Angiotensin System—Conceptual, or a Regulator of Cardiac Function?", *Circulation Research*, 85, (1999), 643-650.

Duan, J., et al., "A Novel Renal Hypertensive Guinea Pig Model for Comparing Different Inhibitors of the Renin-Angiotensin System", *Journal of Pharmacological and Toxicological Methods*, 35(21, (1996), 83-89.

Dzau, V. J., "Implications of Local Angiotensin Production in Cardiovascular Physiology and Pharmacology", *The American Journal of Cardiology*, 59, (Jan. 23, 1987), 59A-65A.

Elbashir, S. M, "Duplexes of 21-Nucleotide RNAs Mediate RNA Interference in Cultured Mammalian Cells", *Nature*, 411, (2001), 494-498.

Endo-Mochizuki, Y., et al., "Expression of Renin and Angiotensin-Converting Enzyme in Human Hearts", *Heart and Vessels*, 10(6), (1995), 285-293.

Evin, G., et al., "Synthesis of Peptides Related to the Prosegment of Mouse Submaxillary Gland Renin Precursor: An Approach to Renin Inhibitors", *Proc. Natl. Acad. Sci. USA*, 81, (1984), 48-52.

Farrell, D. M., et al., "Angiotensin II Modulates Catecholamine Release Into Interstitial Fluid of Canine Myocardium in vivo", *American Journal of Physiology—Heart and Circulatory Physiology*, 281(12), (2001), H813-H822.

Feoktistov, I., et al., "Mast Cell-Mediated Stimulation of Angiogenesis: Cooperative Interaction Between A$_{2B}$ and A$_3$ Adenosine Receptors", *Circulation Research*, 92(5), (2003), 485-492.

Fleetwood, G., et al., "Involvement of the Renin-Angiotensin System in Ischemic Damage and Reperfusion Arrhythmias in the Isolate Perfused Rat Heart", *Journal of Cardiovascular Pharmacology*, 17(3), (1991), 351-356.

Foucart, S., et al., "Effects of Chronic Treatment With Losartan and Enalaprilat on [$^3$H]-Norepinephrine Release From Isolated Atria of Wistar-Kyoto and Spontaneously Hypertensive Rats", *American Journal of Hypertension*, 9(1), (1995), 61-69.

Frangogiannis, N. G., et al., "Resident Cardiac Mast Cells Degranulate and Release Preformed TNF-α, Initiating the Cytokine Cascade in Experimental Canine Myocardial Ischemia/Reperfusion", *Circulation*, 98(7), (1998), 699-710.

Frangogiannis, N. G., et al., "The Inflammatory Response in Myocardial Infarction", *Cardiovascular Research*, 53, (2002), 31-47.

Fuder, H., et al., "Histamine and Serotonin Released From the Rat Perfused Heart by Compound 48/80 or by Allergen Challenge Influence Noradrenaline or Acetylcholine Exocytotic Release", *Fundamental & Clinical Pharmacology*, 8(6), (Abstract Only), (1994), 477-790.

Galli, S. J., et al., "Genetically Mast-Cell-Defcient W/W$^v$ and SI/SI$^d$ Mice. Their Value for the Analysis of the Roles of Mast Cells in Biologic Responses in vivo", The American *Journal of Pathology*, 127(1), (1987), 191-198.

Gavras, H., et al., "Role of Angiotensin and Its Inhibition in Hypertension, Ischemic Heart Disease, and Heart Failure", *Hypertension*, 37(Part 2), (2001), 342-345.

Geiges, D., et al., "Activation of Protein Kinase C Subtypes α, γ, σ, ε, ζ, and η by Tumor-Promoting and Nontumor-Promoting Agents", *Biochemica Pharmacology*, 53(6), (1997), 865-875.

Gelband, C. H., et al., "Angiotension Receptors and Norepinephrine Neuromodulation: Implications of Functional Coupling", *Regulatory Peptides*, 73, 1998 , 141-147.

Goette, A., et al., "Regulation of Angiotensin II Receptor Subtypes During Atrial Fibrillation in Humans", *Circulation*, 101(23), 2000 , 2678-2681.

Gondo, N., et al., "Angiotensin II Provokes Cesium-Induced Ventricular Tachyarrhythmias", *Cardiovascular Research*, 49, (2001), 381-390.

Goto, M., et al., "Decreased Sensitivity of Distal Nephron and Collecting Duct to Parathyroid Hormone in Pseudohypoparathyroidism Type I", *J. Am. So. Nephrol.* 12(9), (2001), 1965-1970.

Gross, F., et al., "Inhibition of the Renin-Angiotensinogen Reaction by Pepstatin", *Science*, 175, (1972), p. 756.

Gunasegaram, S., et al., "Regulation of Sarcolemmal Na$^+$ / H$^+$ Exchanger Activity by Angiotensin II in Adult Rat Ventricular Myocytes", *Circulation Research*, 85, (1999), 919-930.

Hackenthal, E., et al., "Isorenin, Pseudorenin, Cathespin D and Renin—A Comparative Enzymatic Study of Angiotensin-Forming Enzymes", *Biochimica et Biophysica Acta*, 522, (1978), 574-588.

Hara, M., et al., "Evidence for a Role of Mast Cells in the Evolution to Congestive Heart Failure", *The Journal of Experimental Medicine*, 195(3), (2002), 375-381.

Harada, K., et al., "Angiotensin II Type 1a Receptor Is Involved in the Occurrence of Reperfusion Arrhythmias", *Circulation*, 97, (1998), 315-317.

Harborth, J., "Sequence, Chemical, and Structural Variation of Small Interfering RNAs and Short Hairpin RNAs and the Effect on Mammalian Gene Silencing", *Antisense and Nucleic Acid Drug Development*, 13(2), (2003), 83-105.

Haseloff, J., et al., "Simple RNA Enzymes with New and Highly Specific Endoribonuclease Activities", *Nature*, 334, (1988), 585-591.

Hatta, E., et al., "Activation of Histamine H$_3$ Receptors Inhibits Carrier-Mediated Norepinephrine Release in a Human Model of Protracted Myocardial lschemia", *The Journal of Pharmacology and Experimental Therapeutics*, 283(2), (1997), 494-500.

Hatta, E., et al., "Bradykinin Promotes Ischemic Norepinephrine Release in Guinea Pig and Human Hearts", *The Journal of Pharmacology and Experimental Therapeutics*, 288(3), (1999), 929-927.

Hatta, E., et al., "Serine Protease Enhances Norepinephrine Release and Arrhythmias in Myocardial Ischemia/Reperfusion: Role of Bradykinin and Angiotensin", (Abstract 2789), *Circulation*, 96(8S) (Supplement), Abstracts From the 70th Scientific Sessions, Nov. 9-12, 1997 (Abstract Only), (1997), p. 498-I.

Hidaka, H., et al., "N-(6-Aminohexyl)-5-chloro-1-naphthalenesulfonamide, a camodulin Antagonist, Inhibits Cell Proliferation", *Proc. Nat. Acad. Sci. USA*, 78(7), (1981), 4354-4357.

(56) References Cited

OTHER PUBLICATIONS

Hirabayashi, T., et al., "Localization and Regulation of Cytosolic Phospholipase $A_2$", *Biochimica et Biophysica Acta*, 1488, (2000), 124-138.

Hirsch, A. T., et al., "Active Renin and Angiotensinogen in Cardiac Interstital Fluid After Myocardial Infarction", *American Journal of Physiology—Heart and Circulatory Physiology*, 276(6), (1999), H1818-H1826.

Hosoki, K., et al., "Renin Inhibitory Effect of 2-[4-(4'-Chlorophenoxy)phenoxyacetylamino]-ethyl-phosphorylethanolamine (PE-104) in vitro and in vivo", *The Journal of Pharmacology and Experimental Therapeutics*, 203(2), (1977), 485-492.

Houillier, P., et al., "Signaling Pathways in the Biphasic Effect of Angiotensin II on Apical Na/N Antiport Activity in Proximal Tubule", *Kidney International*, 50, (1996), 1496-1505.

Hugenholtz, P. G., et al., "Nifedipine in the Treatment of Unstable Angina, Coronary Spasm and Myocardial Ischemia", *The American Journal of Cardiology*, 47(1), (Jan. 1981), 163-173.

Humphreys, R. A., et al., "Lack of Involvement of Mast Cell Degranulation in the Antiarrhythmic Effect of Preconditioning in Rats", *Journal of Cardiovascular Pharmacology*, 31(3), (1998), 418-423.

Igarashi, Y., et al., "Characteristics of Histamine Release From Cultured Human Mast Cells", *Clinical and Experimental Allergy*, 26, (1996), 597-602.

Ihara, M., et al., "High Cardiac Angiotensin-II-Forming Activity in Infarcted and Non-Infarcted Human Myocardium", *Cardiology*, 94(4), (2000), 247-253.

Imamura, M., et al., "Activation of Histamine $H_3$-Receptors Inhibits Carrier-Mediated Norephrine Release During Protracted Myocardial Ischemia—Comparision With Adenosine A1-Receptors and alpha sub2-Adrenoceptors", *Circulation Research*, 78, (1996), 475-481.

Imamura, M., et al., "Functional Identification of Histamine $H_3$-Receptors in the Human Heart", *Circulation*, 77, (1995), 206-210.

Irani, A.-M., et al., "Mast Cell Heterogeneity", *Clinical and Experimental Allergy*, 19, (1989), 143-155.

Ito, B. R., et al., "Role of Cardiac Mast Cells in Complement C5a-induced Myocardial Ischemia", *American Journal of Physiology—Heart and Circulatory Physiology*, 264(5), (May 1993), H1346-H1354.

Izumi, H., et al., "Increase of Plasma Renin Activity After Subcutaneous Application of Compound 48/80 in the Rat", *European Journal of Pharmacology*, 109, (1985), 249-256.

Jalowy, A., et al., "$AT_1$ Receptor Blockade in Experimental Myocardial Ischemia/Reperfusion", *Journal of the American Society of Nephrology*, 10(Supp. 11), (Jan. 1999), S129-S136.

Janiszewski, J., et al., "Activation of Rat Peritoneal Mast Cells in Coculture With Sympathetic Neurons Alters Neuronal Physiology", *Brain, Behavior, and Immunity*, 4(2), (Jun. 1990), 139-150.

Jensen, B. L., et al., "Adrenomedullin Stimulates Renin Release and Renin mRNA in Mouse Juxtaglomerular Granular Cells", *Hypertension*, 29, (1997), 1148-1155.

Johren, O., et al., "Localization of Angiotensin-Converting Enzyme, Angiotensin II, Angiotensin II Receptor Subtypes, and Vasopressin in the Mouse Hypothalamus", *Brain Research*, 757, (1997), 218-227.

Jolly, S. R., "Effects of Lodoxamide on Ischemic Reperfused Myocardium", *Journal of Cardiovascular Pharmacology*, 4(3), (1982), 441-448.

Jones, S. E, et al., "Tranilast Reduces Mesenteric Vascular Collagen Deposition and Chymase-Positive Mast Cells in Experimental Diabetes", *Journal of Diabetes and Its Complications*, 18(5), Elsevier science, (Sep. 2004), 309-315.

Julius, S., "Sympathetic Hyperactivity and Coronary Risk in Hypertension", *Hypertension*, 21(6)(Part 2), (1993), 886-893.

Karmazyn, M., et al., "The Myocardial $Na^+$-$H^+$ Exchange—Structure, Regulation, and Its Role in Heart Disease", *Circulation Research*, 85, (1999), 777-786.

Katz, S. A., et al., "Effect of Bilateral Nephrectomy on Active Renin, Angiotensinogen, and Renin Glycoforms in Plasma and Myocardium", *Hypertension*, 30(2)(Part 1), (1997), 259-266.

Keller, A. M., "Acute Reoxygeneration Injury in the Isolated Rat Heart: Role of Resident Cardiac Mast Cells", *Circulation Research*, 63(6), (Dec. 1988), 1044-1052.

Kim, Y.-Y., et al., "Inhibition of Histamine Release From Dispersed Human Lung and Tonsillar Mast Cells by Nicardipine and Nifedipine", *British Journal of Clinical Pharmacology*, 19, (1985), 631-638.

Kitamura, Y., et al., "Decrease of Mast Cells in W / $W^v$ Mice and Their Increase by Bone Marrow Transplantation", *Blood*, 52(2), (1978), 447-452.

Kokubu, T., et al., "Highly Potent and Specific Inhibition of Human Renin by Derivatives of Histidylstatine", Hypertension, 7, (*Abstracts of the Council for High Blood Pressure Research—39th Annual Fall Conference and Scientific Sessions*, Sep. 18-21, 1985), (1985), p. 837.

Kokubu, T., et al., "Highly Potent and Specific Inhibitors of Human Renin", *Biochemical and Biophysical Research Communications*, 118(3), (Feb. 14, 1984), 929-933.

Kotchen, T. A., et al., "In vitro and in viivo Inhibition of Renin by Fatty Acids", *American Journal of Physiology*, 234(6), (1978), E593-E599.

Kounis, N. G., et al., "Unstable Angina, Allergic Angina, and Allergic Myocardial Infarction", *Circulation*, 100(25), (1999), p. 156e.

Koyama, M., et al., "Increased Severity of Reperfusion Arrhythmias in Mouse Hearts Lacking Histamine H3-Receptors", *Biochemical and Biophysical Research Communications*, 306(3), (2003), 792-796.

Koyama, M., et al., "Norepinephrine Release From the Ischemic Heart is Greatly Enhanced in Mice Lacking Histamine $H_3$ Receptors", *Molecular Pharmacology*, 63(2), (2003), 378-382.

Kruger, P. G., et al., "Response of Rat Myocardial Mast Cells to Experimental Ischemia", *Journal of Experimental Pathology*, 5, (1990), 29-38.

Kubler, W., et al., "Signal Transduction in Myocardial Ischaemia", *European Heart Journal*, 15(4), (1994), 437-445.

Kurz, T., et al., "Alphas-Adrenergic System and Arrhythmias in Ischaemic Heart Disease", *European Heart Journal*, 12 (Supplement F), (1991), 88-98.

Kushiku, K., et al., "Upregulation of Immunoreactive Angiotensin II Release and Angiotensinogen mRNA Expression by High-Frequency Preganglionic Stimulation at the Canine Cardiac Sympathetic Ganglia", *Circulation Research*, 88(1), (2001), 110-116.

Laine, P., et al., "Adventitial Mast Cells Connect With Sensory Nerve Fibers in Atherosclerotic Coronary Arteries", *Circulation*, 101(14), (2000), 1665-1669.

Lazarus, B., et al., "The Role of Mast Cells in Ischaemia-Reperfusion Injury in Murine Skeletal Muscle", *Journal of Pathology*, 191, (2000), 443-448.

Levi, R., et al., "Chapter 21. Histamine-Mediated Cardiac Effects", *In: Drug-Induced Heart Disease*, Bristow, M. R., Editor, Elsevier/North-Holland Biomedical Press, Amsterdam, The Netherlands, (1980), 377-395.

Levi, R., et al., "Histamine $H_3$-Receptors: A New Frontier in Myocardial Ischmia", The *Journal of Pharmacology and Experimental Therapeutics*, 292(3), (2000), 825-830.

Lin, R. C., et al., "Mechanisms of Synaptic Vesicle Exocytosis", *Annual Review of Cell and Developmental Biology*, 16, (2000), 19-49.

Lindpaintner, K., et al., "The Cardiac Renin-Angiotensin System—An Appraisal of Present Experimental and Clinical Evidence", *Circulation Research*, 68(4), (1991), 905-921.

Ma, X., et al., "Angiotensin Selectively Activates a Subpopulation of Postganglionic Sympathetic Neurons in Mice", *Circulation Research*, 88(8), (2001), 787-793.

Machida, T., et al., "Tissue-Plasminogen Activator Releases Norepinephrine From Sympathetic Nerves Via a Plasmin- and Plasminogen-Independent Mechanism", (Abstract 1407), *Circulation*, 100(17) (Supplement), (2004), III293-III294.

(56) References Cited

OTHER PUBLICATIONS

Markwell, M. A. K., et al., "A Modification of the Lowry Procedure to Simplify Protein Determination in Membrane and Lipoprotein Samples", *Analytical Biochemistry*, 87, (1978), 206-210.

Marone, G., et al., "Immunological Characterization and Functional Importance of Human Heart Mast Cells", *Immunopharmacology*, 31(1), Elsevier Science, (Nov. 1995), 1-18.

Martin, S., et al., "Pathogenesis of low dose streptozotocin induced diabetes in mice", requirement for α1-adrenoreceptor activation and vasoactive amine release, *Diabetologia*, vol. 32, (1989), 140-142.

Martiny-Baron, G., et al., "Selective Inhibition of Protein Kinase C Isozymes by the Indolocarbazole Gö 6976", *The Journal of Biological Chemistry*, 268(13), (1993), 9194-9197.

Maruyama, R., et al., "Angiotensin-Converting Enzyme-Independent Angiotensin Formation in a Human Model of Myocardial Ischemia: Modulation of Norepinephrine Release by Angiotensin Type 1 and Angiotensin Type 2 Receptors", *The Journal of Pharmacology and Experimental Therapeutics*, 294(1), (2000), 248-254.

Maruyama, R., et al., "Norepinephrine Release and Ventricular Fibrillation in Myocardial Ischemia/Reperfusion: Roles of Angiotensin and Bradykinin", *Journal of Cardiovascular Pharmacology*, 34, (1999), 913-915.

McDonald, R. L., et al., "The Effect of the Angiotensin II ($AT_{1a}$) Receptor Stably Transfected Into Human Neuroblastoma SH-SY5Y Cells on Noradrenaline Release and Changes in Intracellular Calcium", *Neuroscience Letters*, 199, (1995), 115-118.

Meisler, David, et al., "Cromolyn Treatment of Giant Papillary Conjunctivitis", *Arch Ophthalmal*, 100(10), (1982), 1608-1610.

Merrifield, R. B, "Solid Phase Peptide Synthesis. I. The Synthesis of a Tetrapeptide", *The Journal of the American Chemical Society*, 85(14), (Jul. 20, 1963), 2149-2154.

Misono, K. S., et al., "Characterization of the Active Site of Mouse Submaxillary Gland Renin", *Biochemistry*, 19, (1980), 2616-2622.

Miyazaki, M., et al., "Synthetic Phosphatidylethanolamines as Renin Inhibitors (39832)", *Proceedings of the Society for Experimental Biology and Medicine*, 155, (1977), 468-473.

Müller, D. N., et al., "Local Angiotensin II Generation in the Rat Heart—Role of Renin Uptake", *Circulation Research*, 82(1), (1998), 13-20.

Musgrave, I. F., et al., "Effect of Phorbol Ester and Pertussis Toxin on the Enhancement of Noradrenaline Release by Angiotensin II in Mouse Atria", *British Journal of Pharmacology*, 96(3), (Mar. 1989), 609-616.

Nakaie, C. R., et al., "Inhibition of Renin by Conformationally Restricted Analogues of Angiotensinogen", *The Biochemical Journal*, 205, (1982), 43-47.

Neves, S. R., et al., "G. Protein Pathways", *Science*, 296(5573), (May 31, 2002), 1636-1639.

Nguyen, G., et al., "Pivotal Role of the Renin/Prorenin Receptor in Angiotensin II Production and Cellular Responses to Renin", *The Journal of Clinical Investigation*, 109(11), (Jun. 2002), 1417-1427.

Nguyen, G., et al., "The Renin Receptor: The Facts, the Promise and the Hope", *Curr. Opin. Nephrol. Hypertens.*, 12, (2003), 51-55.

Nilsson, G., et al., "Phenotypic Characterization of the Human Mast-Cell Line HMC-1", *Scandinavian Journal of Immunology*, 39(5), (1994), 489-498.

O'Rourke, S. T, "Nitro vasoliators: Pharmacology and use in the Treatment of Myocardial Ischemia", *American Jounal of Pharmaceutical Education*, 66, (Feb. 14, 2002), 177-180.

Pang, X., et al., "A Neurotensin Receptor Antagonist Inhibits Acute Immobilization Stress-Induced Cardiac Mast Cell Degranulation, a Corticotropin-Releasing Hormone-Dependent Process", *The Journal of Pharmacology and Experimental Therapeutics*, 287 (1), (1998), 307-314.

Parenteau, G. L, et al., "Prevention of Ischemia-Reperfusion Injury by the Allergy Drug Lodoxamide Tromethamine", The Society of Thoracic Surgeons, *Annals of Thoracic Surgery* 52(4), (1991), 832-838.

Parikh, V., et al., "Cardiac Mast Cell Stabilization and Cardioprotective Effect of Ischemic Preconditioning in Isolated Rat Heart", *Journal of Cardiovascular Pharmacology*, 31, (1998), 779-785.

Park, K. H., et al., "Nitric Oxide Is a Mediator of Hypoxic Coronary Vasodilatation—Relation to Adenosine and Cyclooxygenase-Derived Metabolites", *Circulation Research*, 71(4), (1992), 992-1001.

Passier, R. C. J. J., et al., "Expression and Localization of Renin and Angiotensinogen in Rat Heart After Myocardial Infarction", *American Journal of Physiology—Heart and Circulatory Physiology*, 271(3), (1996), H1040-H1048.

Patella, V., et al., "Human Heart Mast Cells—Isolation, Purification, Ultrastructure, and Immunologic Characterization", *The Journal of Immunology*, 154(6), (1995), 2855-2865.

Patella, V., et al., "Stem Cell Factor in Mast Cells and Increased Mast Cell Density in Idiopathic and Ischemic Cardiomyopathy", *Circulation*, 97, (1998), 971-978.

Paton, W. D., "Compound 48/80: A Potent Histamine Liberator", *British Journal of Pharmacology*, 6, (1951), 499-508.

Peach, M. J., "Renin-Angiotensin System: Biochemistry and Mechanisms of Action", *Physiological Reviews*, 57(2), (1977), 313-370.

Pedersen, O. D., et al., "Trandolapril Reduces the Incidence of Atrial Fibrillation After Acute Myocardial Infarction in Patients With Left Ventricular Dysfunction", *Circulation*, 100(4), (1999), 376-380.

Poulsen, K., et al., "Competitive Inhibitors of Renin", *Biochemistry*, 12(20), (1973), 3877-3882.

Putney, L. K., et al., "The Changing Face of the $NA^+ / H^+$ Exchanger, NHE1: Structure, Regulation, and Cellular Actions", *Annu. Rev. Pharmacol. Toxicol.*, 42, (2002), 527-552.

Reid, A. C., et al., "Coupling of Angiotensin II $AT_1$ Receptors to Neuronal NHE Activity and Carrier-Mediated Norepinephrine Release in Myocardial Ischemia", *American Journal of Physiology—Heart and Circulatory Physiology*, 286, (Apr. 2004), H1448-H1454.

Reitstetter, R., et al., "Dependence of Nicotinic Acetylcholine Receptor Recovery From Desensitizatioin on the Duration of Agonist Exposure", *The Journal of Pharmacology and Experimental Therapeutics*, 289(2), (1999), 656-660.

Roberts, D. J., et al., "Inhibition of Depolarisation-Evoked [$^3$H]noradrenaline Release From SH-SY5Y Human Neuroblastsoma Cells by Muscarinic (M1) Receptors is Not Mediated by Changes in [$Ca^{2+}$]i", *Molecular Brain Research*, 87, (2001), 81-91.

Rump, L. C., et al., "$β_2$-Adrenergic Receptor and Angiotensin II Receptor Modulation of Sympathetic Neurotransmission in Human Atria", *Circulation Research*, 74(5), (1994), 434-440.

Rump, L. C., et al., "β-Adrenergic, Angiotensin II, and Bradykinin Receptors Enhance Neurotransmission in Human Kidney", *Hypertension*, 26, (1995), 445-451.

Saino, A., et al., "Modulation of Sympathetic Coronary Vasoconstriction by Cardiac Renin-Angiotensin System in Human Coronary Heart Disease", *Circulatiion*, 101(19), (2000), 2277-2283.

Schomig, A., et al., "Catecholamine Release and Arrhythmias in Acute Myocardial Ischaemia", *European Heart Journal*, 12 (Supplement F), (1991), 38-47.

Schomig, A., "Catecholamines in Myocardial Ischemia—Systemic and Cardiac Release", *Circulation*, 82(3) (Supp. II), (Sep. 1990), II-13-II-22.

Schomig, A., et al., "Sympatho-Adrenergic Activation of the Ischemic Myocardium and Its Arrhythmogenic Impact", Hertz, 20(Nr. 3), (1995), 169-186.

Schulman, E. S., "The Role of Mast Cells in Inflammatory Responses in the Lung", *Critical Reviews in Immunology*, 13(1), (1993), 25-70.

Schwertz, D. W., et al., "Changes in Phosphoinositide-Specific Phospholipase C and Phospholipase $A_2$ Activity in Ischemic and Reperfused Rat Heart", *Basic Research in Cardiology*, 87, (1992), 113-127.

Sealey, J. E., et al., "Inhibition of Renin by Heparin", *The Journal of Clinical Endocrinology and Metabolism*, 27, (Jan.-Dec. 1967), 699-705.

Sealey, J. E., "Plasma Renin Activity and Plasma Prorenin Assays", *Clinical Chemistry*, 37 (No. 10(B)), (1991), 1811-1819.

(56) References Cited

OTHER PUBLICATIONS

Serneri, G. G. N., et al., "Evidence for the Existence of a Functional Cardiac Renin—Angiotensin System in Humans", *Circulation*, 94(8), (1996), 1886-1893.

Sesti, C., et al., "Ectonucleotidase in Sympathetic Nerve Endings Modulates ATP and Norepinephrine Exocytosis in Myocardial Ischermia", *The Journal of Pharmacology and Experimental Therapeutics*, 306(1), (2003), 238-244.

Seyedi, N., et al., "Bradykinin Activates a Cross-Signaling Pathway Between Sensory and Adrenergic Nerve Endings in the Heart: A Novel Mechanism of Ischemic Norepinephrine Release?", *The Journal of Pharmacology and Experimental Therapeutics*, 290(2), (1999), 656-663.

Seyedi, N., et al., "Bradykinin $B_2$-Receptor Activation Augments Norepinephrine Exocytosis From Cardiac Sympathetic Nerve Endings—Mediation by Autocrine/Paracrine Mechanisms", *Circulation Research*, 81(5), (1997), 774-784.

Seyedi, N., et al., "Histamine $H_3$-Receptor-Induced Attenuation of Norepinephrine Exocytosis: A Decreased Protein Kinase A Activity Mediates a Reduction in Intracellular Calcium", *The Journal of Pharmacology and Experimental Therapeutics*, 312(1), (first published on the Internet on Aug. 11, 2004; DOI: 10.1124/jpet.104.072504), (2005), 272-279.

Seyedi, N., et al., "Ischemia Promotes Renin Activation and Angiotensin Formation in Sympathetic Nerve Terminals Isolated From the Human Heart: Contribution to Carrier-Mediated Norepinephrine Release", *The Journal of Pharmacology and Experimental Therapeutics*, 302(2), (2002), 539-544.

Silver, R. B., "Chapter 12—Ratio Imaging: Practical Considerations for Measuring Intracellular Calcium and pH in Living Tissue", *Methods in Cell Biology*, vol. 56—Video Microscopy, (1998), 237-251.

Silver, R. B., et al., "Coupling of Histamine $H_3$ Receptors to Neuronal $Na^+$ / $H^+$ Exchange: A Novel Protective Mechanism in Myocardial Ischemia", *Proc. Natl. Acad. Sci.*, 98(5), (Feb. 27, 2001), 2855-2859.

Silver, R. B., et al., "Decreased Intracellular Calcium Mediates the Histamine $H_3$-Receptor-Induced Attenuation of Norepinephrine Exocytosis From Cardiac Sympathetic Nerve Endings", *Proc. Natl. Acad. Sci. USA*, 99(1), (Jan. 8, 2002), 501-506.

Silver, R. B., et al., "Low-NaCl Diet Increases H-K-ATPase in Intercalated Cells From Rat Cortical Collecting Duct", *Am. J. Physiol.*, (1998), F94-F102.

Silver, R. B, et al., "Mast Cells: A Unique Source of Renin", *Proceedings of the National Academy of Sciences of USA*, 101(37), (Sep. 14, 2004), 13607-13612.

Silver, R. B., et al., "Potassium Depletion Increases Proton Pump ($H^+$-ATPase) Activity in Intercalated Cells of Cortical Collecting Duct", *American Journal of Physiology—Renal Physiology*, 279, (2000), F195-F202.

Simoneau, B., et al., "Discovery of Non-Peptidic $P_2$-$P_3$ Butanediamide Renin Inhibitors With High Oral Efficacy", *Bioorganic & Medicinal Chemistry*, 7, (1999), 489-508.

Smith, N. C. E., et al., "LLC-$PK_1$ Cells Stably Expressing the Human Norepinephrine Transporter: A Functional Model of Carrier-Mediated Norepinephrine Release in Protracted Myocardial Ischemia", *The Journal of Pharmacology and Experimental Therapeutics*, 291(2), (1999), 456-463.

Söderholm, H., et al., "Activation of Ras, Raf-1 and Protein Kinase C in Differentiating Human Neuroblastoma Cells After Treatment With Phorbolester and NGF", *Cellular Signalling*, 13, (2001), 95-104.

Spellman, C. W., "Achieving Glycemic Control: Cornerstone in the Treatment of Patients With Multiple Metabolic Risk Factors", S8 *JAOA Supplement 1*, vol. 109, No. 5, Spellman—Achieving Glycemic Control, (May 2009), S8-S13.

Sperr, W. R., et al., "The Human Cardiac Mast Cell: Localization, Isolation, Phenotype, and Functional Characterization", *Blood*, 84(11), (1994), 3876-3884.

Storgaard, T., et al., "Prejunctional Modulation by Angiotensins of Noradrenaline Release From Sympathetic Neurons in Isolated Rabbit Aorta", *Naunyn-Schmiedeberg's Archives of Pharmacology*, 356(6), (1997), 706-711.

Sudhof, T. C., et al., "Synapsins: Mosaics of Shared and Individual Domains in a Family of Synaptic Vesicle Phosphoproteins", *Science*, 245(4925), (Sep. 29, 1989), 1474-1480.

Suzuki, F., et al., "A Rapid and Large-Scale Isolation of Renin From Mouse Submaxillary Gland by Pepstatin-Aminohexyl-Agarose Affinity Chromatography", *The Journal of Biochemistry*, 89(4), (Apr. 1981), 1107-1112.

Szelke, M., et al., "Potent New Inhibitors of Human Renin", *Nature*, 299, (Oct. 7, 1982), 555-557.

Tanaka, T., et al., "Calmodulin Antagonists' Binding Sites on Calmodulin", *Pharmacology*, 26, (1983), 249-257.

Tatar, F. A, et al., "The Effect of Verapamil on Stress-Induced Rat Gastric Musosa", *The Journal of Medical Sciences*, 25(1), (1995), 43-46.

Tharp, M. D., et al., "Confugated Avidin Binds to Mast Cell Granules", *The Journal of Histiochemistry and Cytochemistry*, 33(1), (1985), 27-32.

Theoharides, T. C., et al., "Antiallergic Drug Cromolyn May Inhibit Histamine Secretion by Regulating Phosphorylation of a Mast Cell Protein", *Science*, 207(4426), (Jan. 4, 1980), 80-82.

Theoharides, T. C., et al., "Critical role of mast cells in inflammatory diseases and the effect of acute stress", *Journal of Neuroimmunology*, 146(1-2), (Jan. 2004), 1-12.

Tsien, R. Y., "New Calcium Indicators and Buffers With High Selectivity Against Magnesium and Protons: Design, Synthesis, and Properties of Prototype Structures", *Biochemistry*, 19, (1980), 2396-2404.

Van Kats, J. P., et al., "Angiotensin Production by the Heart—A Quantitative Study in Pigs With the Use of Radiolabeled Angiotensin Infusions", *Circulation*, 98, (1998), 73-81.

Vaughan, P. F. T., et al., "The Use of the Human Neuroblastoma SH-SY5Y to Study the Effect of Second Messengers on Noradrenaline Release", *Gen. Pharmac.*, 26(6), (1995), 1191-1201.

Von Lutterotti, N., et al., "Renin is Not Synthesized by Cardiac and Extrarenal Vascular Tissues—A Review of Experimental Evidence", *Circulation*, 89(1), (Jan. 1994), 458-470.

Wakabayahi, S., et al., "Molecular Physiology of Vertebrate Na+ / H+ Exchangers", *Physiological Reviews*, 77(1), (1977), 51-74.

Walker, M. J. A., et al., "The Lambeth Conventions: Guidelines for the Study of Arrhythmias in Ischaemia, Infarction, and Reperfusion", *Cardiovascular Research*, 22(7), (1988), 447-455.

Wang, P., et al., "Mast Cell Degranulation does not Contribute to Ischemic Preconditioning in Isolated Rabbit Hearts", *Basic Research in Cardiology*, 91(6), (Nov. 1996), 458-467.

Way, K. J., et al., "Identification of PKC-Isoform-Specific Biological Actions Using Pharmacological Approaches", *Trends in Pharmacological Sciences*, 21(5), (2000), 181-187.

Weisser, K., et al., "The Role of Enzyme and Substrate Concentration in the Evaluation of Serum Angiotensin Converting Enzyme (ACE) Inhibition by Enalaprilat in Vitro", *Biochemical Pharmacology*, 42(9), (1991), 1729-1737.

White, N. H, et al., "Effect of prior intensive therapy in type 1 diabetes on 10-year progression of retinopathy in the DCCT/EDIC: comparison of adults and adolescents.", *Diabetes*, 59(5), (May 2010), 1244-1253.

Wienen, W., et al., "Different Types of Receptor Interaction of Peptide and Nonpeptide Angiotensin II Antagonists Revealed by Receptor Binding and Functional Studies", *Molecular Pharmacology*, 41(6), (1992), 1081-1088.

Wong, P. C., et al., "Nonpeptide Angiotensin II Receptor Antagonists. XI. Pharmacology of EXP3174: An Active Metabolite of DuP 753, An Orally Active Antihypertensive Agent", *The Journal of Pharmacology and Experimental Therapeutics*, 255(1), (1990), 211-217.

Wood, J. M., et al., "Structure-Based Design of Aliskiren, a Novel Orally Effective Renin Inhibitor", *Biochemical and Biophysical Research Communications*, 308, (2003), 698-705.

(56) References Cited

OTHER PUBLICATIONS

Yule, D. I., et al., "U73122 Inhibits $Ca^{2+}$ Oscillations in Response to Cholecystokinin and Carbachol but Not to JMV-180 in Rat Pancreatic Acinar Cells", The Journal of Biological Chemistry, 267(20), (1992), 13830-13835.

Zimmerman, B. G., "Effect of Acute Sympathectomy on Responses to Angiotensin and Norepinephrine", Circulation Research, 11, (1962), 780-787.

Zymek, P., et al., "The Mast Cell: A Potential Therapeutic Target in Myocardial Infarction", Drug Design Reviews, 2(3), (May 2005), 219-225.

"International Application Serial No. PCT/US2004/033755, International Search Report dated Dec. 2, 2005", 6 pgs.

"International Application Serial No. PCT/US2004/033755, Written Opinion dated Dec. 2, 2005", 9 pgs.

Beneteau-Burnat, B., et al., "Angiotensin-Converting Enzyme: Clinical Applications and Laboratory Investigations on Serum and Other Biological Fluids",(Abstract), Critical Reviews in Clinical Laboratory Sciences, 28(5-6), 337-356, (1991), 1 pg.

Bicket, Daphne P., "Using ACE Inhibitors Appropriately", American Family Physician, 66(3), (2002), 461-468.

Cobankara, Veli, et al., "Renin and angiotensin-converting enzyme (ACE) as active components of the local synovial renin-angiotensin system in rheumatoid arthritis", Rheumatol. Int., 25, (2005), 285-291.

Engeli, Stefan, et al., "Physiology and Pathophysiology of the Adipose Tissue Renin-Angiotensin System", Hypertension, 35, (2000), 1270-1277.

Fewtrell, C. M. S., et al., "The Effects of Substance P on Histamine and 5-Hydroxytryptamine Release in the Rat", J. Physiol., 330, (1982), 393-411.

Hermann, K., et al., "The Renin-Angiotensin System in Patients with Repeated Anaphylactic Reactions during Hymenoptera Venom Hyposensitization and Sting Challenge", (Abstract), Int Arch Allergy Immunol., 112(3), 251-256, (1997), 1 pg.

Imada, A., et al., "Mast cells correlate with angiogenesis and poor outcome in stage I lung adenocarcinoma", Eur. Respir. J., 15, (2000), 1087-1093.

Izai, Midori, et al., "Prorenin-Renin Axis in Synovial Fluid in Patients with Rheumatoid Arthritis and Osteoarthritis", Endocrinol Japan, 39(3), (1992), 259-267.

Kayaselcuk, Fszilet, et al., "Relationship between gastritis severity, Helicobacter pylori intensity and mast cell density in the antrum and corpus", Turk J Gastroenterol, 13, (2002), 154-158.

Kew, M. C., et al., "Arterial Hypertension as a Paraneoplastic Phenomenon in Hepatocellular Carcinoma", Arch. Intern. Med., vol. 149, (Sep. 1969), 2111-2113.

Lavie, C. J., et al., "Regression of increased left ventricular mass by antihypertensives", (Abstract), Drugs, 42(6). 945-961, (1991), 1 pg.

Lavoie, Julie L., et al., "Minireview: Overview of the Renin-Angiotensin System—An Endocrine and Paracrine System", Endocrinology, 144(6), (2003), 2179-2183.

Leung, P. S., et al., "The renin-angiotensin system and male reproduction: new functions for old hormones", J. Mol. Endocrinol., 30(3), (2003), 263-270.

Lilly, L. S., et al., "Renin Expression by vVscular Endothelial Cells in Culture", Circulation Research, 57(2), (1985), 312-318.

Luciani, J. C., "Chronic hypernatremia, hypovolemia and partial hypopituitarism in sarcoidosis: a case report", (Abstract), Clin. Nephrol., 13(5), 242-247, (1980), 1 pg.

Mackins, Christina J., "Cardia mast cell-derived renin promotes local angiotensin formation, norepinephrine release, and arrhythmias in ischemias/reperfusion", The Journal of Clinical Investigation, 116(4), (2006), 1063-1070.

Matsuo, T., et al., "Mast cell chymase expression in Helicobacter pylori-associated gastritis", Histopathology, 43, (2003), 538-549.

Millar, E. A., et al., "Activity of the renin-angiotensin system in acute severe asthma and the effect of angiotensin II on lung function", Thorax, 49, (1994), 492-495.

Montiel, M., et al., "Renin-angiotensin-aldosterone system in hyper- and hypothyroid rats during sodium depletion", (Abstract), Endocr. Res. Commun., 9(3-4), 249-260, (1982), 1 pg.

Nielsen, A. H., et al., "The Uteroplacental Renin-Angiotensin System", Placenta, 21, (2000), 468-477.

Park, Cheol Park, et al., "Thyroxine treatment induces upregulation of renin-angiotensin-aldosterone system due to decreasing effective plasma volume in patients with primary myxoedema", Nephrology Dialysis Transplation, 16, (2001), 1799-1806.

Peng, Shao-Hua, et al., "Significance and relationship between infiltrating inflammatory cell and tumor angiogenesis in hepatocellular carcinoma tissues", World J Gastroenterol, 11(41), (2005), 6521-6524.

Pesci, Alberto, et al., "Mast Cells in Bronchiolitis Obliterans Organizing Pneumonia—Mast Cells Hyperplasia and Evidence for Extracellular Release of Tryptase", Chest, 110, (1996), 383-391.

Puxeddu, I., et al., "Mast cells in allergy and beyond", The Inernational Journal of Biochemistry & Cell Biology, 35, (2003), 1601-1607.

Ratnam, Samuel, et al., "Mast cell response during the early phase of tuberculosis: an electron-microscopic study", Can. J. Microbiol., 23, (1977), 1245-1251.

Raynolds, M. V., et al., "Angiotensin-converting enzyme DD genotype in patients with ischaemic or idiopathic dilated cardiomyopathy", (Abstract), The Lancet, 342(8879), 1073-1075, (1993), 1 pg.

Reilly, P. M., et al., "Vasoactive mediators and splanchnic perfusion", Crit Care Med., 21(2 Suppl), (1993), S55-S68.

Roberts, I. S. D., et al., "Mast cells: the forgotten cells of renal fibrosis", J. Clin. Pathol., 53, (2000), 858-862.

Rosenblum, W. I., "A Possible Role for Mast Cells in Controlling the Diameter of Arterioles on the Surface of the Brain", Brain Research, 49, (1973), 75-82.

Sernia, Contrad, "A Critical Approach of the Intrinsic Pancreatic Angiotensin-Generating System", J. Pancreas, 2(1), (2001), 50-55.

Spech, H. J., et al., "[Renin-angiotensin system in acute hepatitis (author's transl)]", (Abstract), Leber Magen Darm., 11(1), (1981), 10-14, (1981), 1 pg.

Speth, R. C., et al., "Angiotensin II: a reproductive hormone too?", Regul. Pept., 79(1), (1999), 25-40.

Steckelings, U. M., et al., "The renin-angiotensin-system in the skin—Evidence for its presence and possible functional implications", Experimental Dermatology, 4, (1995), 329-334.

Sugamata, Masao, et al., "Increase of Activated Mast Cells in Human Endometriosis", (Abstract), American Journal of Reproductive Immunology, 53(3), 120-125, (2005), 1 pg.

Sugiyama, Katsumi, "Histamine release from rat mast cells induced by Sendai virus", Nature, 270, (1977), 614-615.

Swales, J. D., et al., "Renin in the Arterial Wall", Clin. Exper. Hypertens. A5(7&8), (1983), 1127-1136.

Tylavsky, F. A., et al., "Plasma renin activity is associated with bone mineral density in premenopausal women", Osteoporosis International, 8(2), (1998), 136-140.

Veerasingham, S. J., et al., "Brain renin—angiotensin system dysfunction in hypertension: recent advances and perspectives", British Journal of Pharmacology, 139, (2003), 191-202.

Volpe, Massimo, et al., "The Renin-Angiotensin System as a Risk Factor and Therapeutic Target for Cardiovascular and Renal Disease", J. Am. Soc. Nephrol., 13(Suppl. 3), (2002), S173-S178.

Walker, M. A., et al., "Inhibition of fibrosis in TSK mice by blocking mast cell degranulation", (Abstract), J. Rheumatol., 14(2), 299-301, (1987), 1 pg.

Weaver-Osterholtz, D., et al., "The Urinary Bladder Angiotensin System: Response to Infusions of Angiotensin I and Angiotensin-Converting Enzyme Inhibitors", American Journal of Kidney Diseases, 28(4), (1996), 603-609.

Weaver-Osterholtz, Dana, et al., "The Bladder Angiotensin System in Female Rates: Response to Infusions of Angiotensin I and the Angiotensin Converting Enzyme Inhibitor Enalaprilat", The Journal of Urology, 165, (2001), 1735-1738.

"U.S. Appl. No. 12/237,176, Non Final Office Action dated Nov. 7, 2013", 19 pgs.

Mapstone, R., et al., "Prevalence of diabetes in glaucoma", British Medical Journal, vol. 291, (1985), 93-95.

(56) References Cited

OTHER PUBLICATIONS

Pichot, O., et al., "Color Doppler flow imaging and orbital and ocular vascularization", (Abstract Only), *Journal Francais d'Opthalmologie*, vol. 19, No. 1, 19-31, (1996), 1 pg.

Sheard, P., "Use of substituted pyran-4-one-2-carboxylic acids or their pharmaceutically useful derivatives in treatment or prevention of the side-effects of diabetes", DE 3112262 (Abstract Only), (1981), 1 pg.

Sorkin, E. M., et al., "Ocular Sodium Cromoglycate", (Abstract and Summary Only), *Drugs*, vol. 31, Issue 2, 131-148, (1986), 7 pgs.

"International Application Serial No. PCT/US2004/033755, International Preliminary Report on Patentability dated", 10 pgs.

"International Application Serial No. PCT/US2004/033755, Invitation to Pay Fees and Partial Search Report mailed".

Church, M. K, et al., "Human ocular mast cells", Curr Opin Allergy Clin Immunol., 2(5), (Oct. 2002), 419-22.

Lopez, R., et al., "Absence of mast cells in diabetic retinopathy", Microvasc Res., 24(1), (Jul. 1982), 87-93.

Ribatti, Domenico, et al., "Neovascularization and mast cells with tryptase activity increase simultaneously in human pterygium", J. Cell. Mol. Med. vol. 11, No. 3, 2007, (2007), 585-589.

"U.S. Appl. No. 12/237,176", 11 Pgs.

"U.S. Appl. No. 12/237,176, Examiner Interview Summary dated Apr. 20, 2011", 3 pgs.

Fan, Bao Jian, et al., "Glaucoma: genes, phenotytpes, and new directions for therapy", The Journal of Clinical Investigation, 120(9), (Sep. 2010), 3064-3072.

\* cited by examiner

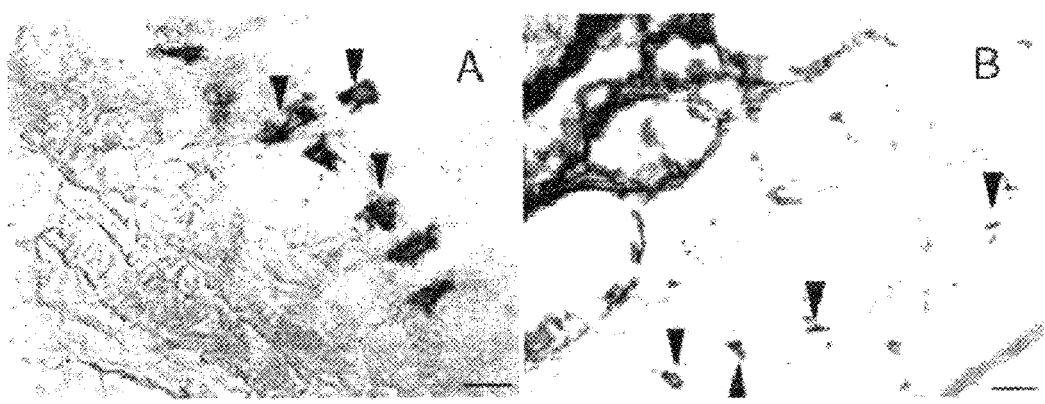
*Fig. 4A*  *Fig. 4B*
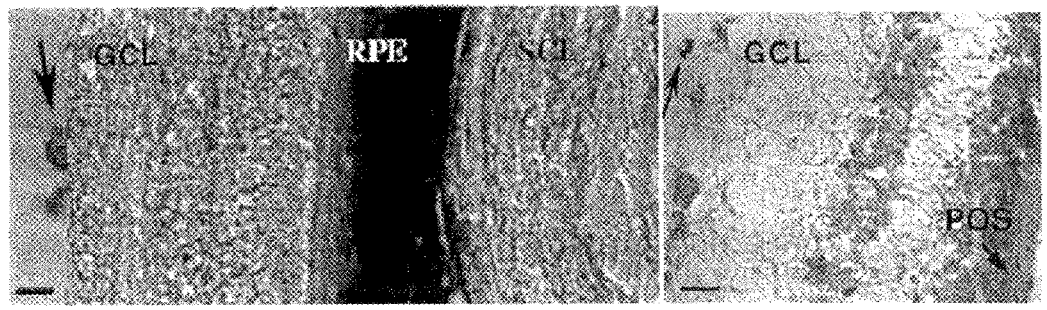
*Fig. 5*
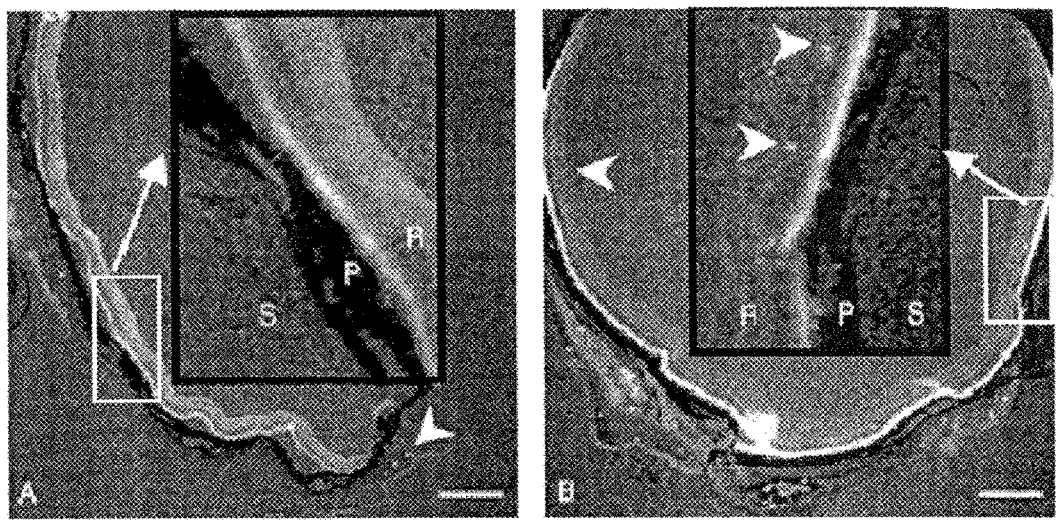
*Fig. 6A*  *Fig. 6B*

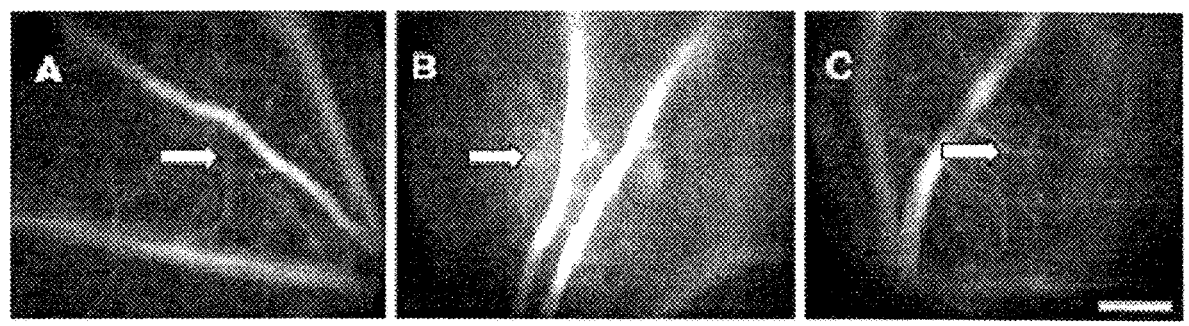
*Fig.15A*  *Fig.15B*  *Fig.15C*
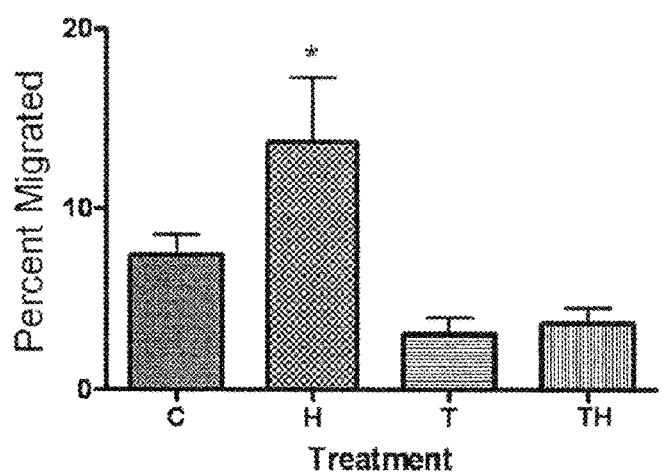
*Fig.16*

MAST CELL INHIBITION IN DISEASES OF THE RETINA AND VITREOUS

This application claims benefit of the filing date of U.S. Provisional Ser. No. 61/060,029, filed Jun. 9, 2008, the contents of which are specifically incorporated herein by reference.

This application is related to U.S. application Ser. Nos. 10/964,567, 11/657,343 and 12/237,176, the contents of which are specifically incorporated herein by reference.

BACKGROUND OF THE INVENTION

Homeostasis of the eye, as in tissues elsewhere in the body, depends on the presence of normal vasculature, extra cellular matrix, and various cell types. If homeostasis is disturbed by infection, inflammation, or metabolic disease, visual function becomes impaired. The end result of these conditions is often fibrosis.

The posterior segment of the eye consists of structures behind the lens; the interior of the back of the eye is filled with vitreous, a viscoelastic material consisting largely of water, collagen, and hyaluronic acid. The vitreous serves as a shock absorber, among other things, for the retina, the most posterior tissue in the eye. In addition, the vitreous can provide scaffolding over which glial and endothelial cells migrate from their normal intraretinal position anteriorly over the retinal surface and/or into the vitreous in certain disease states (e.g., diabetes, proliferative vitreoretinopathy, retinopathy of prematurity). The retina consists of multiple layers of neurons, blood vessels, extra cellular matrix (ECM), and various resident and transient cells such as glial cells and monocytes. The vascular supply of the retina consists of the retinal blood vessels (found in three layers on the innermost portion of the retina) and the choriocapillaris (a rich vascular plexus found in the outermost portion of the retina). The photoreceptors rest on a monolayer of cells, the retinal pigmented epithelium (RPE). The RPE rests on a collagenous basement membrane (Bruch membrane), and directly beneath this structure flows the choriocapillaris, providing blood supply for the outer third of the retina. Although there is a blood-retina barrier and relative immune privilege in this part of the eye, normal inflammatory responses to irritation and hypoxia can be quite robust and can lead to much of the pathology observed in diseases that decrease vision.

The leading cause of vision loss in Americans over the age of 65 is macular degeneration (MD); 12-15 million Americans over the age of 65 have this disease and 10%-15% of them will lose central vision as a direct effect of neovascularization and fibrosis.

Advances in therapeutic options available to treat neovascular macular degeneration have provided some benefit to small subsets of patients with this disease (19, 20). Most drugs currently in clinical trials or approved for treating MD-associated neovascularization are directed at inhibiting promoters of angiogenesis, such as VEGF. Unfortunately, current thinking holds that inhibiting angiogenic cytokines does not address the underlying pathophysiology—ischemia and inflammatory stimuli, and that efforts to minimize sub- and epiretinal fibrosis have met with limited success and that, in any event, such efforts would represent a therapeutic intervention occurring too late to rescue vision, since such scarring would have already led to photoreceptor death.

The leading cause of visual loss for Americans under the age of 65 is diabetes; 6%-8% of the American population is diabetic, and 40,000 patients each year suffer visual loss from complications of the disease, often as a result of retinal edema or neovascularization. Virtually every diabetic has some form of DR after 20 years of the disease. Ischemia occurs as a result of the diabetic microvasculopathy that includes pericyte cell death, microaneurysms, intraretinal microvascular abnormalities, altered vascular permeability, and macular edema. As the hypoxia increases, neovascularization can occur, leading to intraretinal, subhyaloid (between the retinal surface and posterior vitreous base) and vitreous hemorrhage. These proliferating blood vessels are accompanied by fibrosis that occurs as a consequence of glial cell activation and proliferation (gliosis). As abnormal vessels continue to proliferate on the retinal surface, they can extend into the vitreous and contract, causing traction on the retinal surface and leading to retinal detachment, a dreaded complication of proliferative DR. Retinal neovascularization and associated gliosis and fibrosis are also observed in ROP and as a complication of surgery to treat retinal detachment. Surgical intervention and laser obliteration of the peripheral retina (to decrease the metabolic demand and thereby match up supply and demand) are the current treatments and are of limited benefit.

Nowhere in the literature is the case made that mast cells are the source of any of these angiogenic and pro-fibrotic factors that cause diseases of the retina and vitreous. Indeed, the current state of the art in ophthalmology is that mast cells are not found in the privileged space of the retina or vitreous.

SUMMARY OF THE INVENTION

The inventors have made the novel finding that mast cells can be identified in the retina and vitreous, and that they play a key role in retinal vascular leakiness, as well as angiogenic and fibroproliferative diseases of retina and vitreous, and that early intervention can prevent the cycle of destruction that leads to blindness.

One aspect of the invention is a method for treating or inhibiting an ophthalmic retinal vascular permeability, angiogenic or fibroproliferative disease, disorder or condition that involves:

administering to a patient in need thereof a composition that can inhibit mast cell migration into the vitreous or the retina, mast cell proliferation in the vitreous or the retina, or mast cell secretion into the vitreous or the retina, to thereby treat or inhibit an ophthalmic retinal vascular permeability, angiogenic or fibroproliferative disease, disorder or condition.

For example, the ophthalmic abnormal retinal vascular permeability, angiogenic or fibroproliferative disease, disorder or condition can be selected from the group consisting of exudative macular degeneration, dry or wet age-related macular degeneration, retinopathy, diabetic retinopathy, diabetic macular edema (DME), ischemic retinopathy (e.g. retinal vein or artery occlusion), retinopathy of prematurity, proliferative vitreoretinopathy, vitreoretinopathy, scarring of the retina or vitreous or a combination thereof.

When the disease, disorder or condition is diabetic retinopathy, the diabetic retinopathy can be preclinical, nonproliferative or proliferative.

In some embodiments, the composition is administered locally to affected tissues. The affected tissues can, for example, be eye tissues. For example, when the composition is administered locally it can be administered via a contact lens containing the composition, or via a topical solution or gel, or via a stent.

The composition administered can be a sustained release formulation. Moreover, the method can further include administering an inhibitor of a factor secreted by mast cells. Alternatively, the composition to be administered can include an inhibitor of a factor secreted by mast cells. One example of a factor secreted by mast cells is renin. Thus, the methods and compositions described herein can include use of a renin inhibitor. For example, one renin inhibitor that can be used includes a nucleic acid (siRNA) comprising any one of SEQ ID NO:1-8.

The composition can include a mast cell stabilizer that may be administered in the methods of the invention. Examples of mast cell stabilizer that can be employed include lodoxamide, cromolyn, nedocromil, nicardipine, barnidipine, YC-114, elgodipine, niguldipine, R(-)-niguldipine, a dihydropyridine, nicardipine, nifedipine, pemirolast, azelastine, olopatadine, or ketotifen.

In some embodiments, the methods and/or compositions described herein can also include use of an antihistamine, an inhibitor of c-kit receptor, a CXCR antagonist, or a combination thereof. Moreover, the methods and/or compositions described herein can also include use of a combination of mast cell stabilizers, renin inhibitors, AT1R inhibitors, ACE inhibitors, antihistamines, c-kit receptor inhibitors, proteinase inhibitors, or CXCR antagonists.

The composition used in the methods described herein can be administered locally. For example, when local administration is employed the dosages used can be lower than the dosage typically administered systemically for that composition. Moreover, it may also be useful to continuously administer the composition when performing the method describe herein.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 4A-B show toluidine blue-stained mast cells in the posterior pole (FIG. 4A) and anterior pole (FIG. 4B) of a control rat. Scale bar, 20 µm, left and 25 µm, right.

FIG. 5 shows toluidine blue-stained mast cells (arrows) in intact retinal layer as observed in eyes from two diabetic animals (28-days). GCL: ganglion cell layer; RPE: retinal pigment epithelium; SCL: sclera; POS: photoreceptor outer segments. Scale bar, 20 µm, left and 25 µm, right.

FIGS. 6A-B show avidin-FITC labeled mast cells (arrow heads) in the retinal layer as observed in eyes from control (FIG. 6A) and 28-day diabetic (FIG. 6B) animals. S: sclera; P: choroid and retinal pigment epithelium; R: retina. Squared sections are zoomed to see the various layers of the eye. Scale bars, 500 µM.

FIG. 7B', B*) and show retina stained with avidin-FITC and DAPI (A', B') and transmitted light images (A*, B*) (scale bar=20 µcm). FIGS. 7A' and A* are portions of the section shown in FIG. 7A at higher magnification. Similarly, FIGS. 7B' and 7B* show the section in FIG. B at higher magnification.

FIG. 9A shows a schematic diagram of the stratified ocular layers while

FIG. 10C shows an overlay of the avidin and renin fluorescent signals while FIG. 10D is an overlay of the avidin signal (green) with the nuclear dye, DAPI (blue). Scale bars, 15 µm. Note that the avidin labeling identifies mast cells while the anti-renin antibodies indicates that renin is present.

FIGS. 15A-C shows representative angiograms at the same time-point after fluorescein injection and focal plane from a control (FIG. 15A), diabetic (FIG. 15B), and cromolyn-treated diabetic rat (FIG. 15C). Leakage of dye was observed in the eye from the untreated diabetic rat (FIG. 15B). Scale bar, 500 mM.

FIG. 16 graphically illustrates that activation of the histamine $H_4R$ leads to mast cell migration. Chemotaxis experiments were performed with cultured human mastocytoma cells (HMC-1 cells). HMC-1 cells were plated in Corning transwells consisting of inner and outer wells. The number of mast cells migrating through the insert in response to exogenous histamine±thioperamide (an H3/H4 histamine receptor agonist) was counted. The presence of histamine (H) led to significantly more migration ($p<0.05$) compared to control (C), thioperamide (T) alone, or histamine in the presence of thioperamide (TH) treatment.

FIG. 18B) rats. The retinal vasculature was stained with griffonia lectin (green) while the mast cells were stained with avidin-rhodamine (red).

DETAILED DESCRIPTION OF THE INVENTION

Figure 1:
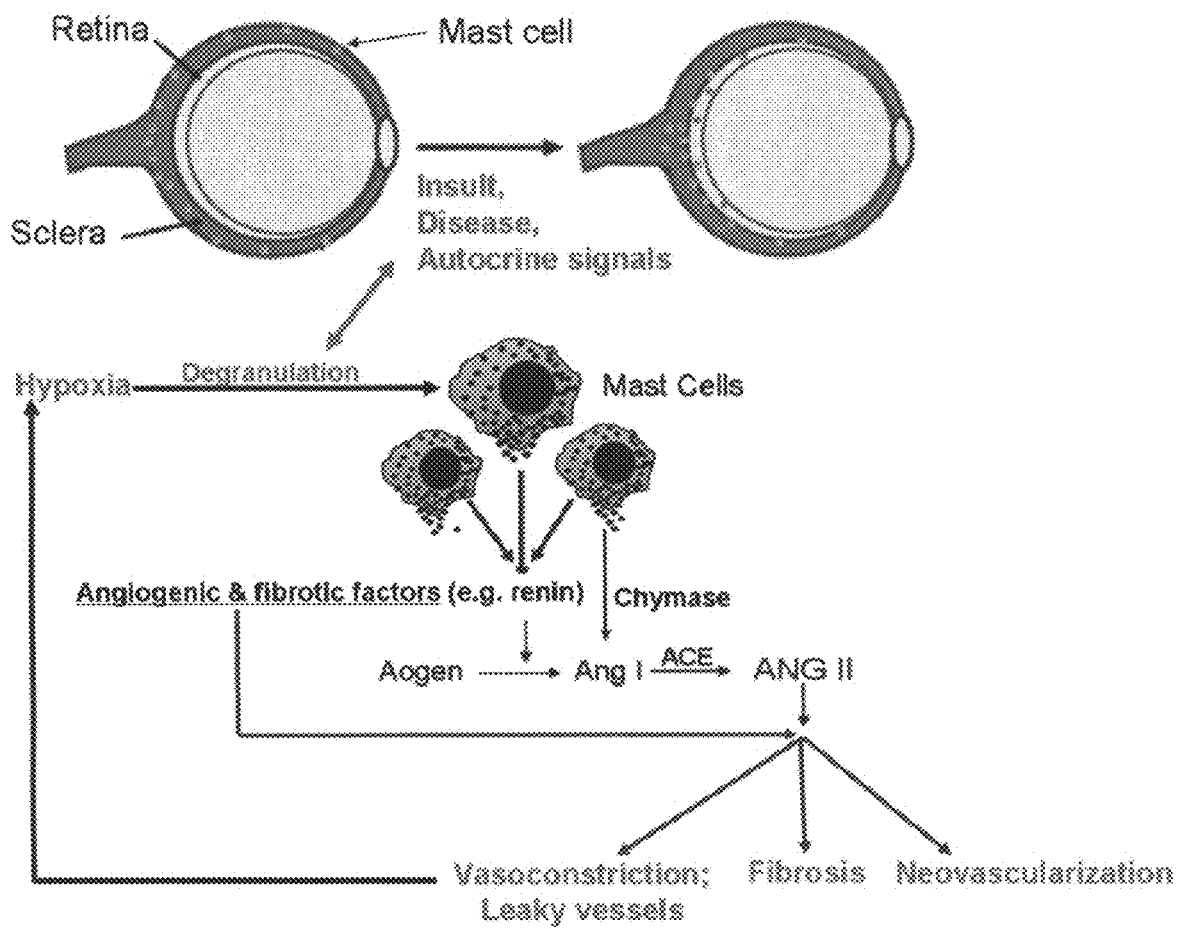
FIG. 1 is a schematic diagram illustrating the migration, proliferation, and degranulation of mast cells observed by the inventors in diseased retina. Mast cells degranulate in response to insult or disease. Positive feedback (on resident mast cells via autocrine signals and paracrine signals from tissues affected by mast-cell-secreted factors; and chemotactic signals attracting precursors) leads to degranulation, mobilization, & proliferation. Mast cells may infiltrate retina and continue the cycle there. This process can unfold slowly, over years, following the initial trigger.

As described herein, mast cells are present in the retina and vitreous. Moreover, the inventors have shown that these mast cells play a key role in retinal vascular leakiness, as well as angiogenic and fibroproliferative diseases of retina and vitreous. According to the invention, early intervention with agents that inhibit mast cell migration, proliferation and/or degranulation within the eye can prevent the cycle of destruction that leads to blindness in persons suffering from retinal diseases, disorders and conditions.

Mast Cells

In the course of proving a hypothesis that mast cell-derived renin (as described in published PCT application WO2005037317, incorporated by reference herein in its entirety) plays a key pathological role in diabetic retinopathy, the inventors have made the surprising discovery that mast cells are found in the immunologically privileged ocular space, and that blocking the migration, proliferation, and degranulation of mast cells into the vitreous and retina can prevent and treat vascular permeability, angiogenic disease, or fibroproliferative disease of the retina and vitreous.

According to the invention, mast cells are present in many tissues, including the retina and vitreous. Mast cells populate other regions of the eye, for example, in the conjunctiva and the choroid (see FIG. 3). But prior to this invention, mast cells were not known to be present in the retina or vitreous, nor were they thought to play a role in diseases of the retina and vitreous (see, e.g., Church M K, McGill J I. "Human ocular mast cells." Curr Opin Allergy Clin Immunol. 2002 October; 2(5):419-22). Indeed a 1982 study looked for mast cells in the retina and found none (Lopez et al. Absence of mast cells in diabetic retinopathy. Microvasc Res. 1982 July; 24(1):87-93.).

Mast cells contain many granules rich in histamine and heparin, and are often identified by their staining characteristics and large granules. Although they are best known for their role in allergy and anaphylaxis, mast cells play an important protective role as well, being intimately involved in wound healing and defense against pathogens.

Mast cells play a role in the inflammatory process. When activated, a mast cell rapidly releases the contents of its granules (degranulation) and various hormonal mediators into the interstitium. Mast cells can be stimulated to degranulate by direct injury (e.g. physical or chemical), cross-linking to immunoglobulin E (IgE) receptors, or by activated complement proteins.

Mast cells express a high-affinity receptor (FcεRI) for the Fc region of IgE. IgE is produced by B cells and, like all antibodies, each IgE specifically binds one antigen. The FcεRI receptor is of such high affinity that binding of IgE molecules is essentially irreversible. As a result, mast cells are coated with IgE.

During allergic reactions, mast cells remain inactive until an allergen binds to an IgE that is associated with the mast cell. Typical allergens are proteins or polysaccharides. It appears that binding of two or more IgE molecules (cross-linking) is required to activate the mast cell. The clustering of the intracellular domains of the cell-bound Fc receptors, which are associated with the cross-linked IgE molecules, causes a sequence of reactions inside the mast cell, ultimately leading to mast cell activation. Although this reaction is most well understood in terms of allergy, it appears to have evolved as a defense system against intestinal worm infestations, and other membrane activation events can either prime mast cells for subsequent degranulation or can act in synergy with FcεRI signal transduction.

Mast cell degranulation can release a variety of molecules into the extracellular environment, including histamine, proteoglycans (e.g., heparin), serine proteases, prostaglandin D2, leukotriene C4 and various cytokines. The inventors have discovered that renin is also released by mast cells upon degranulation.

The inventors have discovered that a cycle of mast cell-related events can occur within the retina that contributes a variety of eye conditions, disorders and diseases. This cycle of mast cell-related events is schematically diagrammed in FIG. 1. FIG. 1 illustrates the migration, proliferation, and degranulation of mast cells in the retina during a disease state. Mast cells degranulate in response to insult or disease. Positive feedback (on resident mast cells via autocrine signals and paracrine signals from tissues affected by mast-cell-secreted factors; and chemotactic signals attracting precursors) leads to degranulation, mobilization, and proliferation. Mast cells infiltrate retina and continue the cycle there. This process can unfold slowly, over years, following the initial trigger, contributing to a variety of conditions, disorders and diseases, as described below in more detail.

Diabetic Retinopathy

Diabetic retinopathy, a complication of diabetes, is the leading cause of blindness in developed countries. It is the most frequent cause of new cases of blindness among adults aged 20-74 years. During the first twenty years of disease, nearly all patients with type I diabetes and >60% of patients with type 2 diabetes have retinopathy. Diabetic retinopathy progresses from mild nonproliferative abnormalities, exemplified by increased vascular permeability, to moderate and severe nonproliferative diabetic retinopathy characterized by vascular closure. Finally, the third stage is proliferative diabetic retinopathy, distinguished by the growth of new blood vessels on the retina and posterior surface of the vitreous.

Macular edema, characterized by retinal thickening from leaky blood vessels, can develop at all stages of retinopathy. Hyperglycemia leads to a wide variety of retinal vascular abnormalities at the microvascular and macrovascular levels.

Evidence indicates that hyperglycemia and tissue hypoxia associated with proliferative diabetic retinopathy lead to an up-regulation of angiogenic factors, including vascular endothelial growth factor (VEGF) and ANG II. Although a causative role for ocular renin-angiotensin system (RAS) in diabetic retinopathy has yet to be fully described, a pathogenic role for the renin-angiotensin system (RAS) in diabetic retinopathy has been actively pursued for the last twenty years. Angiotensin II, the effector peptide of the RAS, possesses potent growth factor properties and promotes neovascularization of the retina, a hallmark of diabetic retinopathy. Additionally, ANG II causes vasoconstriction which promotes hypoxia which in turn can lead to mast cell degranulation. Inhibition of the RAS, with orally administered ACE inhibitors or ARBs, is believed to attenuate many of the vascular abnormalities that develop in diabetic retinopathy. The efficacy of such systemic treatment is currently being evaluated in a large-scale five year randomized clinical trial (Diabetic Retinopathy Candesartan Trial (DIRECT-2002-2007) designed to establish whether treatment with the ARB, candesartan cilexetil, provides effective protection against the onset and progression of diabetic retinopathy. Clearly, the precedent exists for targeting the RAS in slowing the progression of diabetic retinopathy. However, no precedent exists for targeting mast cells in diabetic retinopathy.

| Stage | Morphological (Physical) Changes | Functional Changes |
| --- | --- | --- |
| 1. Preclinical | Small but significant changes can be observed in electroretinograms, but not in a routine retinal exam. | Patients cannot detect any vision changes. Color and/or contrast sensitivity is minimally decreased in some patients, but this is detectable only by specialized instruments. |
| 2. Nonproliferative | Small hemorrhages (bleeding) and microaneurisms (bulging vessels) occur in tiny retinal blood vessels. These changes are visible only in an eye exam, when the pupils are dilated. If vessels begin to leak, the leaking fluid and lipid may collect in the macula, a condition called "macular edema." (This occurs in 25% of diabetics.) | Some individuals perceive no vision changes. Macular edema, if present, may cause difficulties with reading and other activities involving close vision. |
| 3. Proliferative | Retinal blood vessels become occluded (plugged) and the retina loses its oxygen and nutrient supply. The retina responds by growing fragile new blood vessels (neovascularization) which take an abnormal course across the retina. These vessels can break and bleed into the vitreous, preventing light from reaching the retina. Macular edema may be evident. | Spotty or cloudy vision. |
| 4. Late Proliferative | The retina grows more abundant new blood vessels, glial scars may be evident, and the retina may even detach. Fluid in the vitreous and/or macular edema may also be present. | Severe vision loss, culminating in legal blindness in the affected eye(s). There are no known methods of treating or reversing diabetic retinopathy at this stage. |

The human eye contains a resident population of mast cells located primarily in the uvea with a large number of mast cells located in the capillary layer comprising the inner part of the choroid. Data provided herein on eyes from STZ-induced untreated diabetic rat demonstrate mast cell infiltration of the retina/vitreous; ocular compartments that do not normally contain mast cells.

Mast cells degranulate in response to insult or disease. Positive feedback (on resident mast cells via autocrine signals and paracrine signals from tissues affected by mast-cell-secreted factors; and chemotactic signals attracting precursors) leads to a cycle of degranulation, mobilization and proliferation. Mast cells infiltrate retina and continue the cycle there. This process can unfold slowly, over years, following the initial trigger.

By way of example and not limiting the invention, one factor secreted by mast cells, for example, is renin. Renin is a factor in the abnormalities in the microvascular circulation that characterize diabetic retinopathy and other diseases of the back of the eye. As described herein (e.g., see FIG. 1), a paracrine pathway is involved in the initiation of intra-renal RAS and intra-ocular RAS is activated in the eye. Activation of this pathway results in vasoconstriction, excessive norepinephrine (NE) release from sympathetic nerves, and fibrosis. In diabetes, tissue ischemia/hypoxia leads to mast cell degranulation and renin release. Renin binds to the extracellular surface of nearby cell membranes, making renin available to Aogen. After renin acts on Aogen thus forming ANG I, ANG I is converted to ANG II by ACE. The resultant ANG II can then interact with AT1R present in cells of the vasculature and sympathetic nerves in the ocular vasculature and retina. Local production of ANG II, triggered by release of mast cell-derived renin, exerts multiple effects via AT1R activation. These include an increase in vascular resistance and increased sympathetic activity, both of which reduce blood flow, and promotion of fibrosis. Vasoconstriction and interstitial fibrosis then act by exacerbating the initial ischemic insult, and provoke additional local ANG II generation. Thus renin released during mast cell degranulation in response to ischemia/hypoxia in diabetes is a pivotal event in the activation of a local ocular RAS- and is a causative factor of diabetic retinopathy.

Retina and Vitreous

Figure 3:
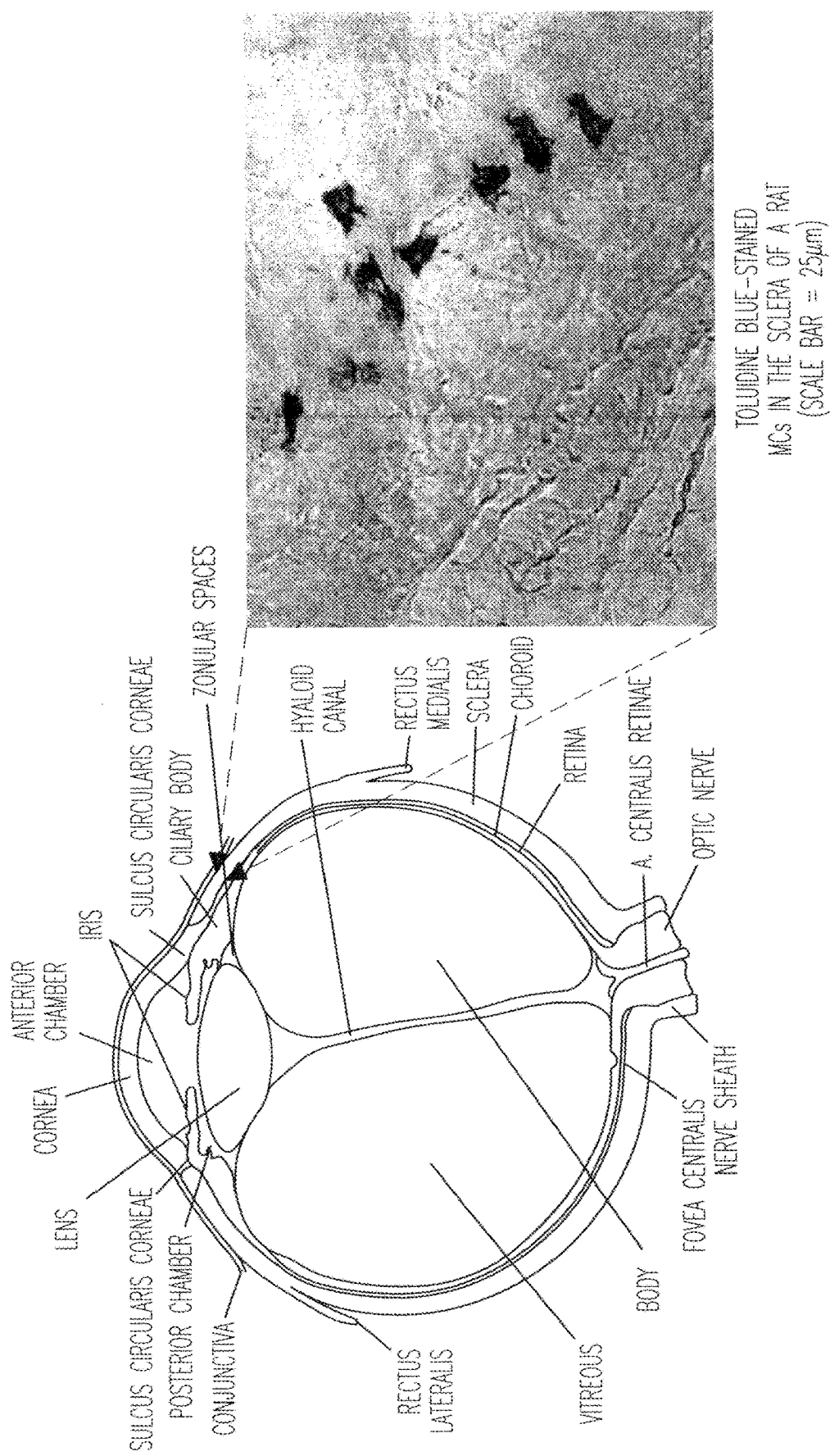
FIG. 3 shows a schematic diagram of the eye (left panel) showing where the toluidine blue-stained mast cells (right panel) were located within the sclera of a rat (scale bar=25 µm).
Figure 7A:
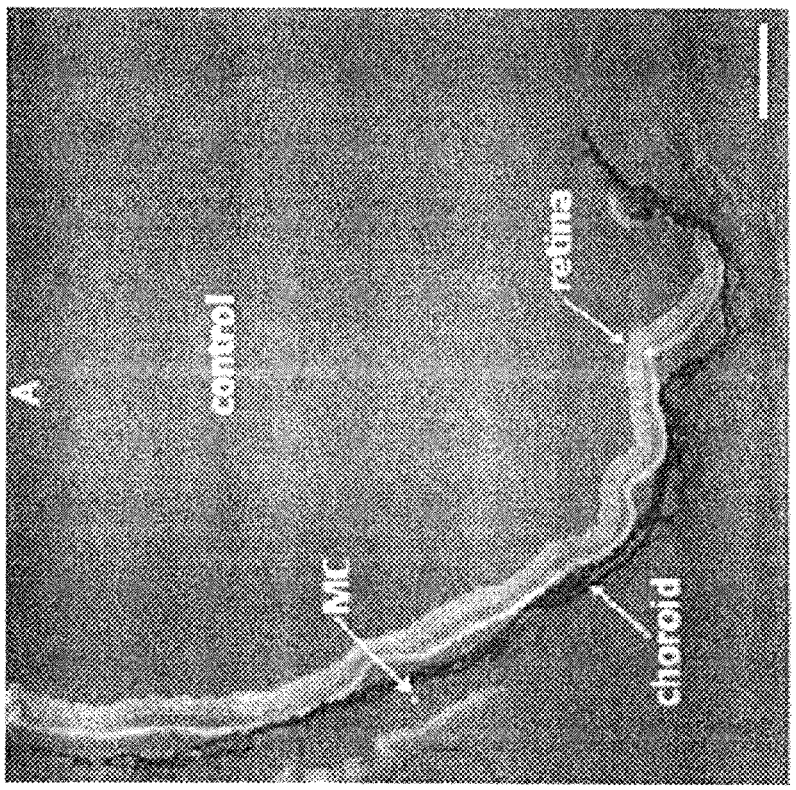
FIG. 7A-B shows avidin-positive mast cells in control (FIG. 7A) and diabetic (FIG. 7B) rat eyes viewed at low magnification (scale bar=500 µm). Note the lack of mast cells near the retina in the control rat. Corresponding insets are at higher magnification (FIGS. 7A' and A*.
Figure 7B:
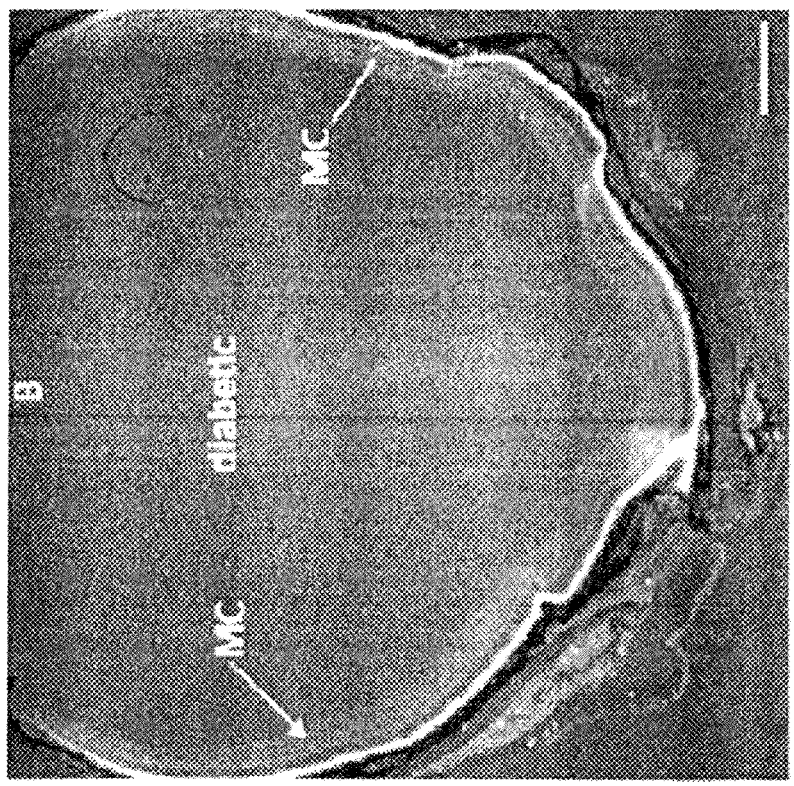
Figure 7A:
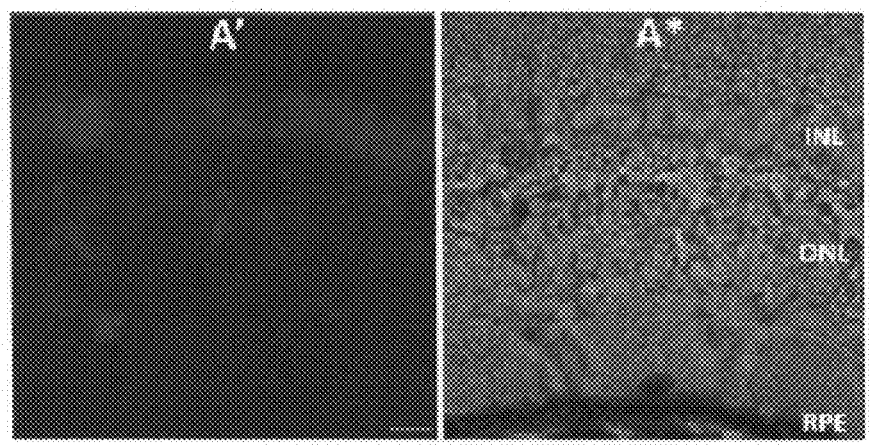
Figure 7B:
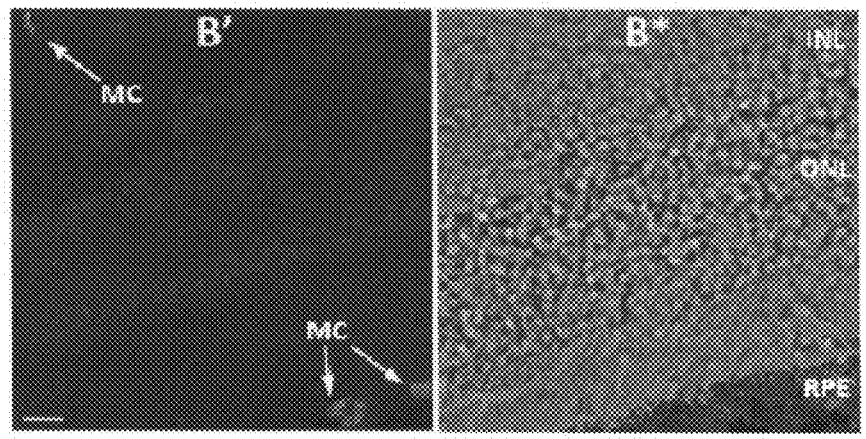

FIG. 3 shows a schematic diagram of the eye. In adult humans the entire retina is about 22 mm in diameter. An area of the retina is the optic disc, sometimes known as "the blind spot" because it lacks photoreceptors. It appears as an oval white area of ~3 mm². Temporal (in the direction of the temples) to this disc is the macula. At its center is the fovea, a pit that is most sensitive to light and is responsible for sharp central vision. The central retina and then the peripheral retina extend around the fovea. The edge of the retina is defined by the ora serrata.

The vertebrate retina has ten distinct layers. From innermost to outermost, they include:
Inner limiting membrane—Müller cell footplates;
Nerve fiber layer;
Ganglion cell layer—Layer that contains nuclei of ganglion cells and gives rise to optic nerve fibers;
Inner plexiform layer;
Inner nuclear layer;
Outer plexiform layer—In the macular region, this is known as the Fiber layer of Henle;
Outer nuclear layer;
External limiting membrane—Layer that separates the inner segment portions of the photoreceptors from their cell nuclei;
Photoreceptor layer—Rods/Cones; and
Retinal pigment epithelium.

The vitreous is the transparent, colorless, gelatinous mass that fills the space between the lens of the eye and the retina lining the back of the eye. It is often referred to as the vitreous body or simply "the vitreous." It contains very few cells (mostly phagocytes which remove unwanted cellular debris in the visual field), no blood vessels, and 99% of its volume is water with salts, sugars, and a network of collagen fibers with hyaluronic acid accounting for the rest.

Diseases to be Treated

A variety of diseases can be treated by using agents that modulate mast proliferation and degranulation. Such diseases include ophthalmic abnormal retinal vascular permeability, angiogenic or fibroproliferative disease, disorder or conditions including exudative macular degeneration, dry or wet age-related macular degeneration, retinopathy, diabetic retinopathy, diabetic macular edema (DME), ischemic retinopathy (e.g. retinal vein or artery occlusion), retinopathy of prematurity, proliferative vitreoretinopathy, vitreoretinopathy, and scarring of the retina and vitreous.

Compounds for Compositions and Methods

A variety of compounds and agents can be used in the compositions and methods of the invention, including renin-angiotensin system (RAS) inhibitors (e.g., AT1R inhibitors, ACE inhibitors, renin inhibitors and the like), mast cell stabilizers, inhibitors of mast cell proliferation and/or migration (antihistamines, CXCR antagonists, c-kit inhibitors, protease inhibitors, and the like. These compounds and agents are described in more detail below.

RAS Inhibitors

AT1R Inhibitors: The invention further contemplates administering compounds that inhibit angiotensin type 1 receptor activity. A number of angiotensin type 1 receptor inhibitors are available. For example, valsartan, olmesartan, candesartan, irbesartan, losartan, EXP3174, telmisartan or other available inhibitors of angiotensin type 1 receptor activity can be used.

ACE Inhibitors: The invention further contemplates administering compounds that inhibit Angiotensin-Converting Enzyme (ACE). A number of ACE inhibitors are available. For example, enalaprilat, captopril, zofenopril, ramipril, quinapril, perindopril, lisinopril, benazepril, fosinopril, or other available inhibitors of ACE activity can be used.

Renin Inhibitors: Renin inhibitors that can be used in the invention include any renin inhibitor available to one of skill in the art. Renin inhibitors that can be used in the invention include, for example, BILA2157, aliskiren, remikiren, ankiren and enalkiren. Aliskiren, is a recently described, novel and orally-effective renin inhibitor. See Wood et al., Biochem. Biophys. Res. Comm., 308(4):698-705. Aliskiren, is available from Speedel Pharma in Basel, Switzerland. Other examples of renin inhibitors are described in published PCT application WO2005037317, incorporated by reference.

For example, small interfering RNAs (siRNA) targeted against renin transcripts were used to specifically reduce renin expression in HMC-1 mast cells Actual siRNAs used to inhibit the functioning of renin mRNA had the following sequences:

```
GAGAAAGGCTGGACAGAGA     (SEQ ID NO: 1)

TCAACTGGCTGGCCTCTTA     (SEQ ID NO: 2)
```

```
GTACAGCACTTTTCTATTT      (SEQ ID NO: 3)

GCAAAGAGAGTACATAACA      (SEQ ID NO: 4)
```

In addition, siRNAs with SEQ ID NOs:4-8 can also be used to reduce rennin expression.

Further information on siRNAs useful for inhibiting expression of rennin is provided in published PCT application WO2005037317, which is specifically incorporated herein by reference in its entirety.

Mast Cell Stabilizers

Mast cells are a normal component of the connective tissue and play an important role in immediate (type I) hypersensitivity and inflammatory reactions by secreting a large variety of chemical mediators from storage sites in their granules upon stimulation.

According to the invention, any mast cell stabilizer can be used. Examples include lodoxamide, cromolyn sodium, nedocromil, nicardipine, barnidipine, YC-114, elgodipine, niguldipine and R(−)-niguldipine. Dihydropyridines, such as nicardipine and nifedipine have been shown to inhibit histamine release from human lung and tonsillar cells (Kim et al., Inhibition of Histamine Release from Dispersed Human Lung and Tonsillar Mast Cells by Nicardipine and Nifedipine, British Journal of Clinical Pharmacology, volume 19, pages 631-638 (1985)).

Because the damage caused by mast cell degranulation, and the concomitant mobilization, recruitment, and proliferation of mast cells, builds up slowly over years, the chronic, low-dose administration of mast cell stabilizers is a preferred embodiment of the invention.

Agents that Inhibit Mast Cell Proliferation and Migration

Antihistamines:

Histamine acts as an autocrine and paracrine mediator and as a chemo-attractant for mast cells, acting through the $H_4$ receptor on mast cells. (FIG. 16). Histamine is released from mast cells in response to $H_1$ receptor activation on mast cells. Therefore anti-histamines inhibit mast cell proliferation and migration. Antihistamines include compounds that selectively or nonselectively inhibit histamine receptors, and include azelastine, oxatomide, terfenadine, epinastine and astemizole, diphenhydramine, loratadine, desloratadine, meclizine, quetiapine, fexofenadine, cimetidine, famotidine, ranitidine, ABT-239, cipralisant, ciproxifan, clobenpropit, thioperamide and/or agents that selectively inhibit (e.g., selectively inhibit) a histamine receptor, including $H_4$ and $H_1$ receptors.

CXCR Antagonists:

CXC chemokine receptors are integral membrane proteins that specifically bind and respond to cytokines of the CXC chemokine family. They represent one subfamily of chemokine receptors, a large family of seven transmembrane G protein-linked receptors. There are currently seven known CXC chemokine receptors in mammals, named CXCR1 through CXCR7. CXCR1 and CXCR2 (also known as IL8RB; CD182; IL8RA; CDw128b; CMKAR2; IL8R2) are expressed on surface of mast cells. Mast cells migrate and are precursors recruited by CXC chemokines with the ELR tripeptide motif, such as IL-8, GRO-a, NAP-2, and ENA-78. CXCR2 antagonists are known in the art. Some non-limiting examples include: SB 225002 (J Biol Chem 273(17): 10095-10098, Apr. 24, 1998); SB 265610 (JPET 299:90-95, 2001) certain nicotinamide N-oxides (Bioorganic & Medicinal Chemistry Letters 11(14): 1951-1954); certain Phenol-containing antagonists of the CXCR2 receptor (Expert Opinion on Therapeutic Patents (18)6: 629-637); certain imidazolylpyrimidines (Bioorg Med Chem. Lett. 2006 May 15; 16(10):2724-8).

C-Kit Inhibitors:

The c-kit proto-oncogene encodes a transmembrane tyrosine kinase receptor. Activation of c-kit by stem cell factor (SCF, also called kit ligand) its natural ligand, promotes its dimerization and autophosphorylation at specific tyrosine residues Tyr567 and Tyr719. Signaling by c-kit plays an important role in cellular transformation and differentiation, including proliferation, survival, adhesion, and chemotaxis of several cell types (including mast cells). Agents that inhibit the activation of c-kit are "c-kit inhibitors" and are known in the art, and include imatinib; 2-phenylaminopyrimidine derivative STI571 (available from Novartis; see, Attoub et al, Cancer Research 62, 4879-4883, Sep. 1, 2002); compounds disclosed in Wisniewski D, Cancer Res. 2002 Aug. 1; 62(15):4244-55 (incorporated herein by reference) including PD173955 and PD180970; and compounds disclosed in Published PCT application WO/2003/002114, incorporated herein by reference.

Proteinase Inhibitors

A crucial step in the movement of mast cells into the privileged space of the eye is the production and activity of specific extracellular proteinases, including the matrix metalloproteinases (MMPs) and the serine proteinase, uPA (urokinase plasminogen activator) and its receptor, uPAR (urokinase plasminogen activator receptor). The interaction of these proteinases and their inhibitors is also implicated in the regulation of angiogenesis and has been widely studied. Other investigators have shown in an animal model of ischemia-induced retinal neovascularization that specific proteinases (MMP-2, MMP-9, and urokinase plasminogen activator) are up-regulated in the retina of mice with experimentally induced retinal neovascularization. A similar up-regulation of proteinases was observed in human epiretinal neovascular membranes from patients with proliferative diabetic retinopathy. (see Das et al Lab Invest 2003, 83:1637-1645). Therefore inhibitors of MMPs, uPA, or uPAR are also useful for inhibiting mast cell movement into the retina and vitreous. Such agents are known in the art.

Administration

The compounds of the invention, including their salts, are administered so as to achieve a reduction in at least one symptom associated with an indication or disease. For example, the compounds described herein can be formulated for administration to reduce at least one symptom of diabetic retinopathy and/or diabetic nephropathy.

To achieve the desired effect(s), the compounds may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, the compound or peptide chosen, the disease, the weight, the physical condition, the health, the age of the mammal, whether prevention or treatment is to be achieved, and if the peptide is chemically modified. Such factors can be readily determined by the clinician employing animal models or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the compounds of the invention may be essentially continuous over a preselected period of time or may be in a series of spaced doses. The terms "continuously administered" or "chronically administered" means maintaining an approximately steady state level of therapeutic composition of the invention throughout the course of the treatment period. This can be accomplished by constantly or repeatedly administering substantially identical amounts of the therapeutic composition of the invention, e.g., at least every hour, 24 hours a day, seven days a week, or through the use of implanted device, such that an approximately steady state level is achieved for the duration of treatment. Both local and systemic administration is contemplated.

To prepare the composition, compounds are synthesized or otherwise obtained, purified as necessary or desired and then lyophilized and stabilized. The compound or peptide can then be adjusted to the appropriate concentration, and optionally combined with other agents. The absolute weight of a given compound or peptide included in a unit dose can vary widely. For example, about 0.01 to about 2 g, or about 0.1 to about 500 mg, of at least one peptide or compound of the invention, or a plurality of compounds and/or peptides specific for a particular mast cell type or renin isotype can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the compounds and peptides of the invention can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

Thus, one or more suitable unit dosage forms comprising the therapeutic compounds of the invention can be administered by a variety of routes including oral, parenteral (including subcutaneous, intravenous, intramuscular and intraperitoneal), rectal, dermal, transdermal, intrathoracic, intrapulmonary and intranasal (respiratory) routes. The therapeutic peptides may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

"Low dose" is an amount which for a given period of time is less than or equal to amounts used in traditional treatment over such a time period, and may be 90% to 1% of the dose traditionally administered.

When the therapeutic compounds of the invention are prepared for oral administration, they are generally combined with a pharmaceutically acceptable carrier, diluent or excipient to form a pharmaceutical formulation, or unit dosage form. For oral administration, the peptides may be present as a powder, a granular formulation, a solution, a suspension, an emulsion or in a natural or synthetic polymer or resin for ingestion of the active ingredients from a chewing gum. The active peptides may also be presented as a bolus, electuary or paste. Orally administered therapeutic compounds and peptides of the invention can also be formulated for sustained release, e.g., the compounds and/or peptides can be coated, micro-encapsulated, or otherwise placed within a sustained delivery device. The total active ingredients in such formulations comprise from 0.1 to 99.9% by weight of the formulation.

By "pharmaceutically acceptable" it is meant a carrier, diluent, excipient, and/or salt that is compatible with the other ingredients of the formulation, and not deleterious to the recipient thereof.

Pharmaceutical formulations containing the therapeutic compounds of the invention can be prepared by procedures known in the art using well-known and readily available ingredients. For example, the compound or peptide can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the compounds of the invention can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one compound or peptide of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more peptides or compounds of the invention are designed to resist disintegration in the stomach and dissolve in the more neutral to alkaline environment of the duodenum.

The therapeutic compounds of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic peptides or compounds of the invention can also take the form of an aqueous or anhydrous solution or dispersion, or alternatively the form of an emulsion or suspension or salve.

Thus, the therapeutic compounds may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelf life of the dosage form. The active peptides and other ingredients may form suspensions, solutions, or emulsions in oily or aqueous vehicles, and may contain formulatory agents such as suspending, stabilizing and/or dispersing agents. Alternatively, the active peptides and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add, if necessary, an adjuvant chosen from antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

Additionally, the compounds are well suited to formulation as sustained release dosage forms and the like. Such sustained release formulations can be administered locally to specific tissues or organs. The formulations can also be constituted so that they release the active peptide or compound, for example, in a particular part of the intestinal or respiratory tract, possibly over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

For topical administration, the therapeutic agents may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic agents of the invention can be delivered via patches or bandages for dermal administration. Alternatively, the peptide or compound can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active peptides and compounds can also be delivered via iontophoresis, e.g., as disclosed in U.S. Pat. No. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the therapeutic peptides or compounds in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic compounds may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

The compounds of the invention can also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific infection, indication or disease. Any statistically significant attenuation of one or more symptoms of an infection, indication or disease that has been treated pursuant to the method of the present invention is considered to be a treatment of such infection, indication or disease within the scope of the invention.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newman, S.

P. in *Aerosols and the Lung*, Clarke, S. W. and Davia, D. eds., pp. 197-224, Butterworths, London, England, 1984).

Therapeutic compounds of the present invention can also be administered in an aqueous solution when administered in an aerosol or inhaled form. Thus, other aerosol pharmaceutical formulations may comprise, for example, a physiologically acceptable buffered saline solution containing between about 0.1 mg/ml and about 100 mg/ml of one or more of the peptides or compounds of the present invention specific for the indication or disease to be treated. Dry aerosol in the form of finely divided solid peptide or particles of selected compounds that are not dissolved or suspended in a liquid are also useful in the practice of the present invention. Peptides and compounds of the present invention may be formulated as dusting powders and comprise finely divided particles having an average particle size of between about 1 and 5 μm, alternatively between 2 and 3 μm. Finely divided particles may be prepared by pulverization and screen filtration using techniques well known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating the particular condition, indication or disease since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic peptides of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic agent may also be administered via nose drops, a liquid spray, such as via a plastic bottle atomizer or metered-dose inhaler. Typical of atomizers are the Mistometer (Wintrop) and the Medihaler (Riker).

Furthermore, the active ingredients may also be used in combination with other therapeutic agents, for example, pain relievers, anti-inflammatory agents, antihistamines, antimicrobials, bronchodilators and the like, whether for the conditions described or some other condition.

The present invention further pertains to a packaged pharmaceutical composition for controlling the symptoms of a particular condition or disease such as a kit or other container. The kit or container holds a therapeutically effective amount of a pharmaceutical composition for controlling the selected condition and instructions for using the pharmaceutical composition for control of the condition. The pharmaceutical composition includes at least one compound or peptide of the present invention, in a therapeutically effective amount such that condition is controlled.

Example 1: Diabetic Retinopathy: Mast Cells and Local RAS

Figure 2:
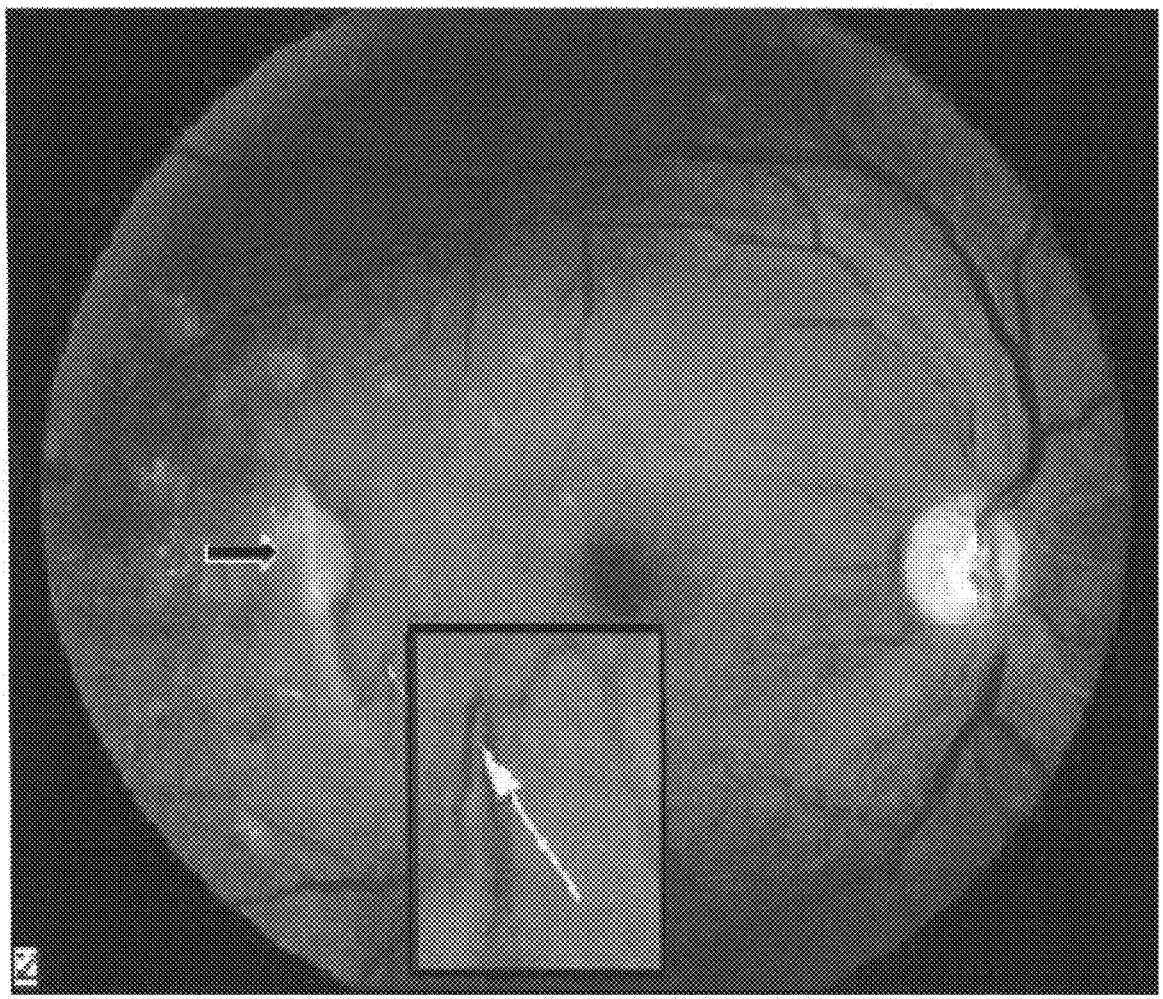
FIG. 2 shows a fundus photograph of the inferior temporal quadrant of the right eye of a patient suffering proliferative diabetic retinopathy. Neovascularization is present as indicated by the vessel at the right arrow. This vessel is growing into the vitreous. This patient also has a fibrotic plaque as indicated by the black arrow.

FIG. 2 is a fundus photograph of the inferior temporal quadrant of the right eye of a patient suffering from proliferative diabetic retinopathy. This area is marked by neovascularization into the vitreous cavity (white arrow) with subsequent fibrosis (black arrow). Lipid exudates (yellow granules) and dot blot hemorrhaging are also present. Data presented below illustrates the role of mast cells, mast cell renin, and a local ocular RAS in diabetic retinopathy.

Example 2: The STZ-Diabetic Rat Model

Investigations into cellular mechanisms involved in development of diabetic retinopathy have been compromised by scarcity of human tissue and lack of animal models. Most diabetic rodent models exhibit only early retinal changes such as pericyte loss, capillary dilatation and leakage, as well as increased basement membrane thickening. To circumvent this, investigators have relied on non-diabetic models of retinal neovascularization that, like proliferative diabetic retinopathy, depend on hypoxia as the stimulus for new growth of blood vessels.

However, for the experiments described herein, an animal model of diabetic retinopathy was used—Long Evans rats developed by Taconic Farms. All experiments were performed in compliance with the ARVO Statement for the Use of Animals in Ophthalmic and Vision Research. To induce a model of type-I diabetes, Sprague Dawley and Long-Evans rats were injected with a single dose of streptozotocin (STZ) (60 mg/kg) and maintained for 2 months. Hyperglycemia was confirmed by monitoring blood from tail bleeds.

To assess vascular leakage in these diabetic rats, fluorescein retinal angiography was performed weekly over a 2-month time course in the Long-Evans rats. In some experiments, rats were treated with the mast cell stabilizer, Na-cromolyn, topically administered to the eyes. The structure of Na-Cromolyn is shown below.

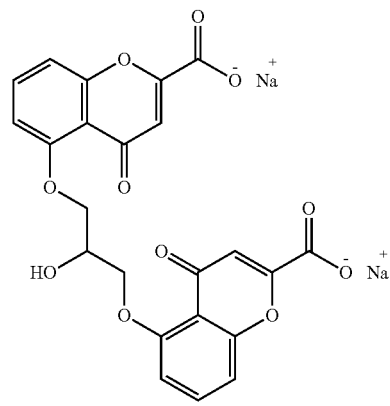

Angiography was performed on an upright fluorescence microscope using a long working distance lens. At the 2-month end point, rats were sacrificed and the eyes were enucleated, dissected free of cornea and extra-orbital connective tissue, and fixed in 4% paraformaldehyde.

For immunocytochemical analyses of mast cell number and distribution, eyes were frozen and cryo-sectioned (5 μm). Mast cells were identified in these sections either with toluidine blue, the classic histochemical stain for mast cells, or immunocytochemically with avidin conjugated to either FITC or rhodamine (Vector Lab). Avidin is a specific marker of mast cells (Bergstresser et al., 1984). Mast cells were also screened for renin using a polyclonal anti-renin antibody, kindly provided by D. Catanzaro, Weill Cornell Medical College.

Example 3: Location of Mast Cells in Diabetic Retinopathy

Localization of ocular mast cell was next determined in eyes from control and STZ-induced diabetic rats. Fixed and frozen sections (10 µM) were initially stained with toluidine blue, the classic histochemical stain for mast cells.

FIG. 4 shows typical staining of mast cells in the eye from a non-diabetic control animal. Mast cells were found in the posterior pole in the sclera (FIG. 4A) and the anterior pole near the ciliary body (FIG. 4B). In contrast, eyes from the diabetic rats displayed a different pattern. In addition to the locations observed in healthy, non-diabetic, mast cells were consistently observed within the retina (n=6).

Toluidine blue staining of the eye from a 28-day diabetic rat is shown in FIG. 5. Mast cells were found opposed to the vitreous near the retinal ganglion cell layer as indicated by the arrows. To further verify that mast cells are found in the retina and vitreous, sections were stained with FITC-avidin; avidin is a highly selective marker for mast cells.

FIGS. 6 and 7 show low magnification (2×) images of 10 µm frozen sections from control (FIGS. 6A and 7A) and diabetic (FIGS. 6B and 7B) rat eyes. The sections were stained with avidin conjugated to fluorescein. Ocular layers are labeled: R (retina), P (retinal pigment epithelium and choroid), and S (sclera). White arrowheads indicate mast cells. In the control eye (FIGS. 6A and 7A), mast cells were found only in the outer scleral region (see arrow head, bottom right hand corner)—no mast cells were observed in the retinal/vitreous layers of these control eyes.

In the diabetic eye ((FIGS. 6B and 7B), however, mast cells were found both in the uvea/scleral layers as well as in the retinal layers, verifying the observations with toluidine blue (FIG. 5). Corresponding insets at a higher magnification (FIG. 7C panels labeled as A', A*, B', B*) show retina stained with avidin-FITC and DAPI (FIG. 7C panel A', FIG. 7 panel B') and transmitted light images (FIG. 7 panel A*, FIG. 7 panel B*). These sections were analyzed this at higher magnification to confirm that the bright dots viewed at low power were avidin-stained mast cells.

Figures 8A, 8B:
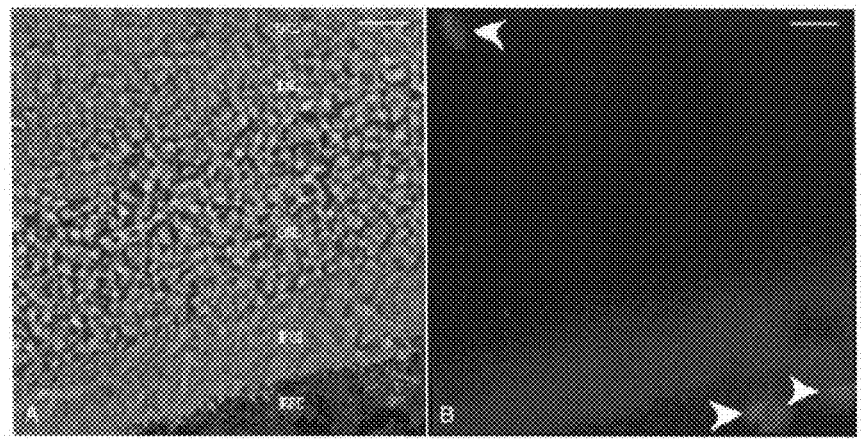
FIG. 8A is a transmitted light image of the corresponding avidin-labeled mast cells shown in FIG. 8B from a 28-day diabetic animal. Scale bars, 20 µm. Approximate retinal layers labeled from top to bottom are: GCL (ganglion cell layer), INL (inner nuclear layer), ONL (outer nuclear layer), POS (photoreceptor outer segments), and RPE (retinal pigment epithelium).

FIG. 8A is a labeled transmitted light image while FIG. 8B is the corresponding immuno-fluorescence image showing avidin labeling. Note the avidin-positive cells (FIG. 8B) in the retinal pigmented epithelium (RPE) (arrow heads) and ganglion cell layer (GCL). These results indicate that mast cells are present in the retina/vitreous layers in the eyes of STZ-induced diabetic rats.

Figure 9B:
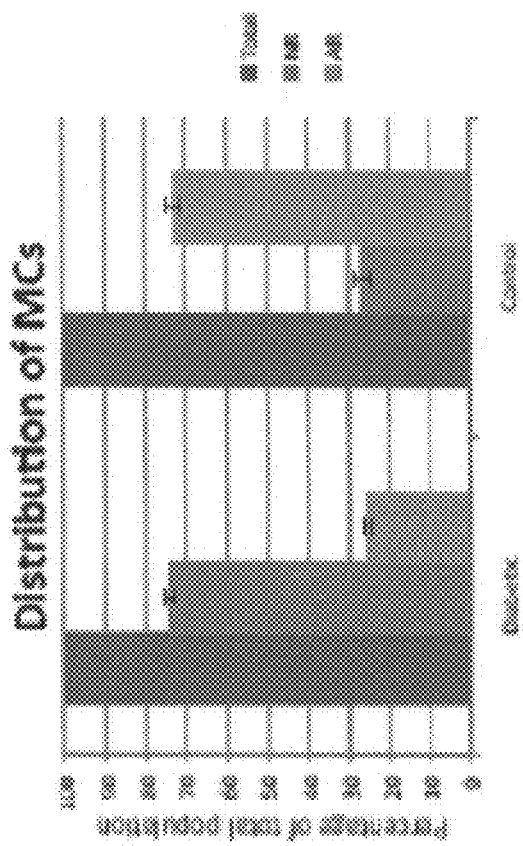
FIG. 9B is graph of the number of avidin-positive mast cells observed in these layers in control and diabetic rat eyes. The distribution of mast cells near (NR), and away from (AR) is illustrated in FIG. 9A and graphically shown for retina from control and diabetic rat eyes. The numbers are expressed as the percentage of cells near (NR), or away from (AR), the retina divided by the total number of avidin-positive mast cells in the ocular sections (e.g., 100*[NR/(NR+AR)]). The total number of mast cells was similar in control and diabetic eyes (186 control (n=3) vs. 182 diabetic (n=3)) but the percentage of mast cells near the retina was significantly higher in diabetic rat eyes.
Figure 9A:
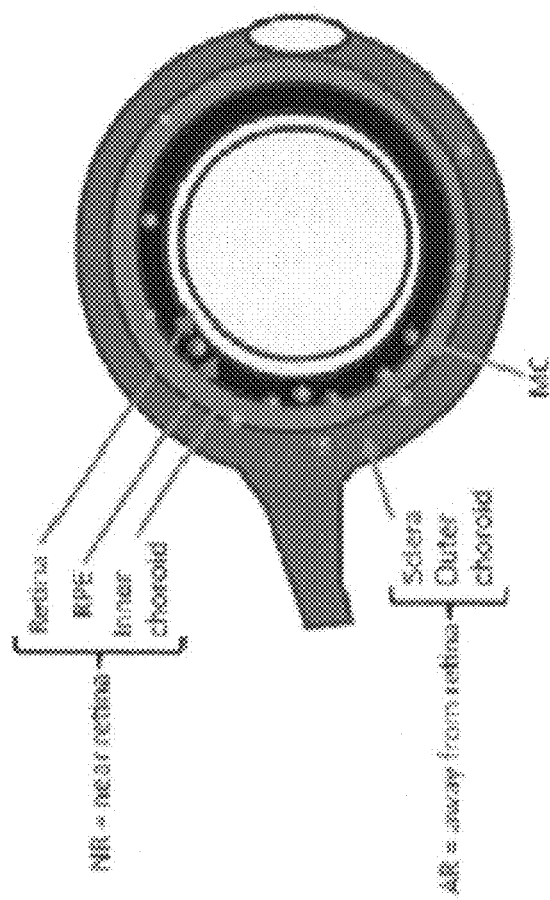

The number and spatial distribution of mast cells was also analyzed. As shown in FIG. 9, there are differences between the diabetic and control eyes. At the 2-month time point the total number of avidin-positive mast cells increased in the ciliary body and anterior sclera of the diabetic rats (24±8 mast cells/section, STZ, n=3; vs. 9±0.3 mast cells/section, con, n=3). This trend was also observed in the sections at the interface between choroid and RPE (23±9 mast cells/section, STZ vs. 12±0.4 mast cells/section, con). In both STZ and control sections, the population of mast cells remained constant in the posterior sclera (11±2 mast cells/section, STZ vs. 10±4 mast cells/section, con). Avidin-positive mast cells were renin-positive, indicating that the renin-angiotensin system (RAS) has a role in diabetic retinopathy.

Figure 18A:
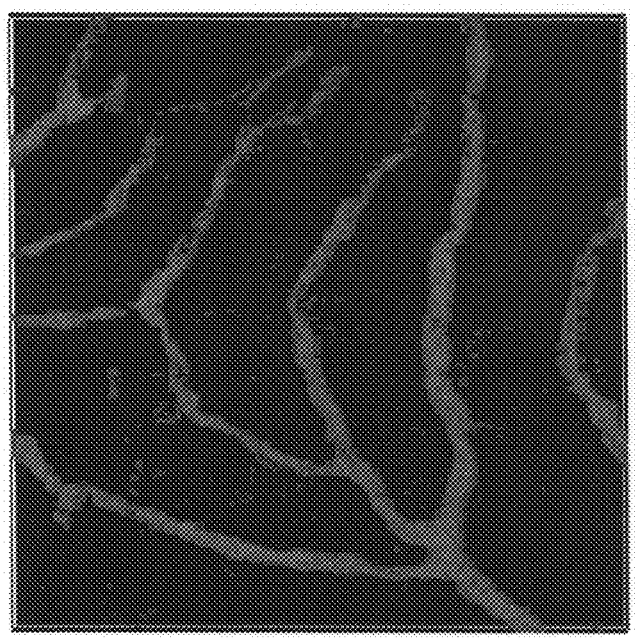
FIG. 18A-B shows that mast cells are not associated with retinal vasculature in healthy non-diabetic (control) animals as illustrated by retinal whole mount (28 days) from saline injected (FIG. 18A) and diabetic (STZ-injected.
Figure 18B:
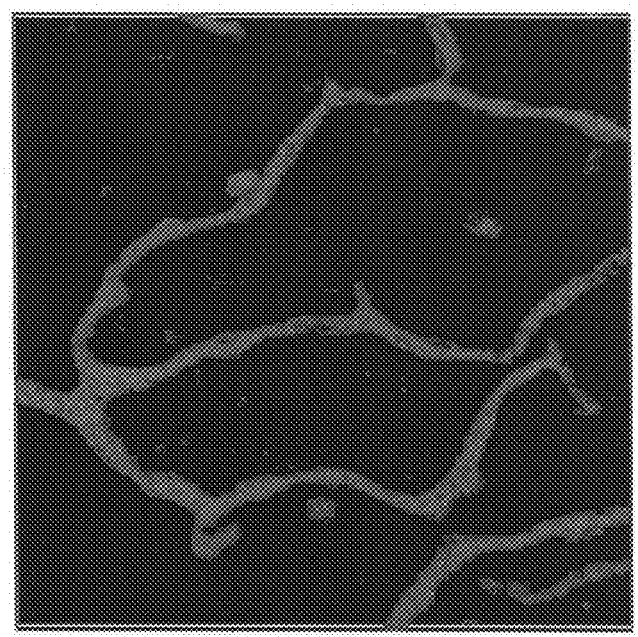

To confirm that mast cells are not associated with retinal vasculature under control conditions, rat retinal whole mounts were examined at 28 days after saline injection (FIG. 18A, control) and STZ-injection (FIG. 18B). Mast cells were not associated with retinal vasculature in control retina (FIG. 18A), but were associated with retinal vasculature in diabetic retina (FIG. 18B). This is evident from the staining patterns observed—retinal vasculature was stained with griffonia lectin and mast cells were stained with avidin-rhodamine.

Example 4: Ocular Mast Cells Express Renin

Figures 10A, 10B, 10C, 10D:
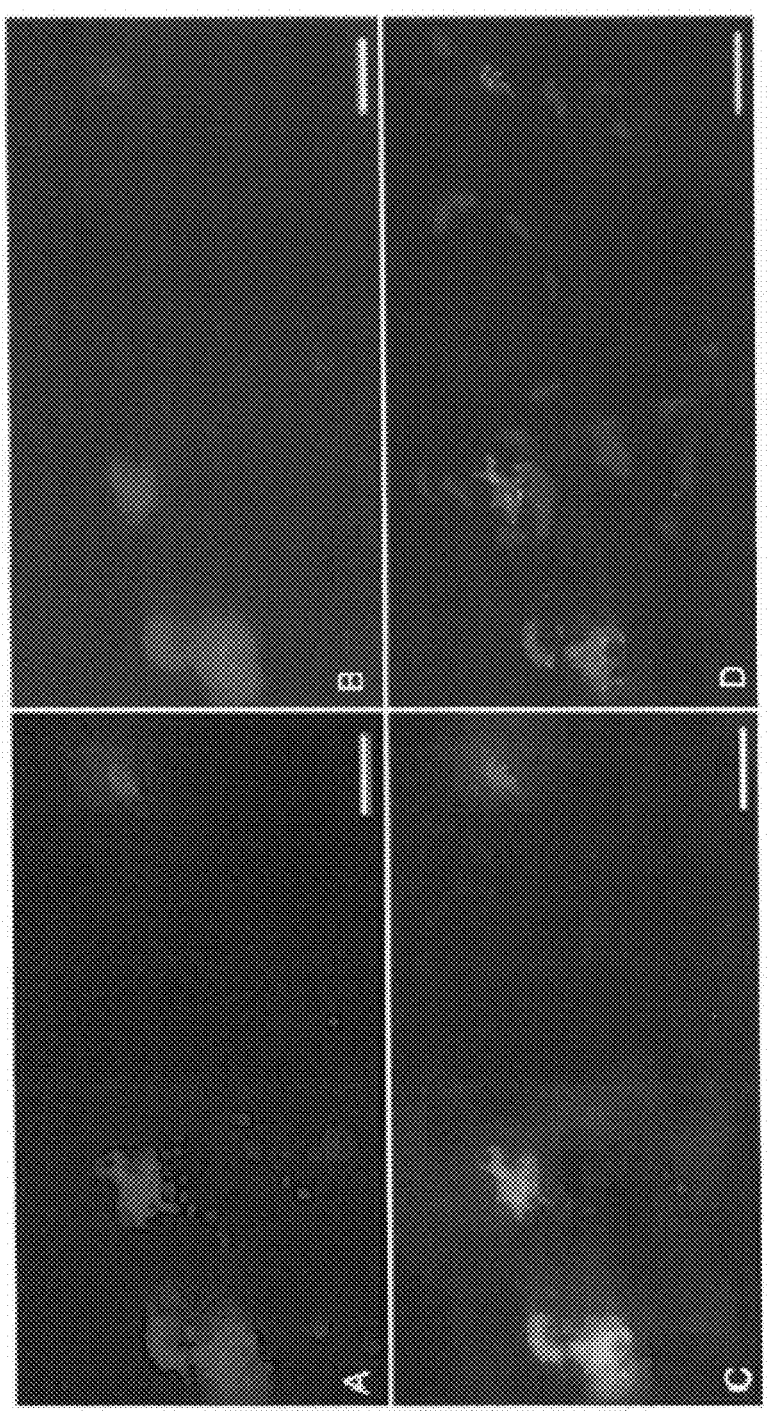
FIG. 10A-D shows avidin- (FIG. 10A) and renin- (FIG. 10B) positive mast cells in a 10 µm thick frozen eye section from the sclera of a 28-day diabetic animal.
Figure 11:
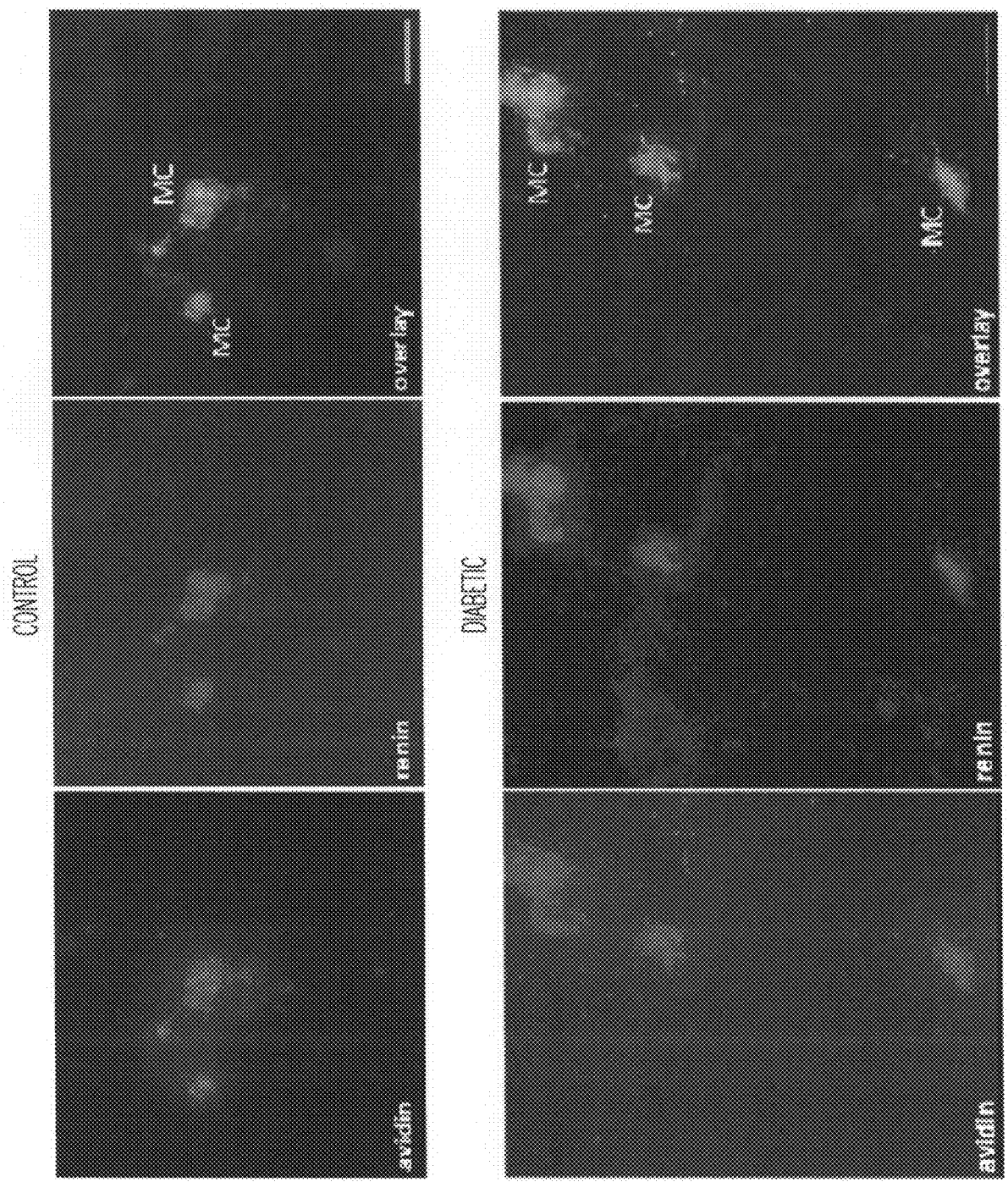
FIG. 11 is a section of an eye from a control (top row) and a 2-month old diabetic (bottom row) rat co-labeled with FITC-avidin (green; identifying mast cells), anti-renin-Ab (red), and displayed in an overlay with DAPI (blue) (scale bar=25 cm).

Immuno-staining for renin was performed on rat eyes to determine whether ocular mast cells express renin. FIG. 10 shows images of sclera from a 29-day old diabetic rat. FIG. 11 shows images of sclera from a 2 month old diabetic rat as well as images of sclera from a control rat. The sclera shown in FIGS. 10 and 11 are labeled with both avidin-conjugated to FITC (green) and renin-conjugated to rhodamine (red). FIG. 10A shows that avidin-positive mast cells are present in the eye and FIG. 10B shows these mast cells are immuno-positive for renin, which is confirmed by the FIG. 10C overlay of the avidin and renin staining. Note that renin is not fully co-localized with the avidin signal, indicating some spatial separation. FIG. 10D is an overlay of the avidin labeling and the nuclear stain, DAPI.

Ocular Mast Cells Migrate to the Retina. As illustrated by the chemotaxis experiments described below, mast cells that are normally found in uvea and choroids (see FIG. 3), migrate to the retina/vitreous layer in rats with STZ-induced diabetic retinopathy.

Chemotaxis experiments were performed with cultured human mastocytoma cells. HMC-1 cells were plated in Corning transwells consisting of inner and outer wells. The number of mast cells migrating through the insert in response to exogenous histamine±thioperamide, an H3/H4 histamine receptor agonist, was counted. The presence of histamine (H) led to significantly more migration (p<0.05) compared to control (C), thioperamide (T) alone, or histamine in the presence of thioperamide (TH) treatment (FIG. 16).

Selective recruitment of mast cells to the retina is due to directed migration of mast cells within the eye. Histamine acts as an autocrine mediator and as a chemo-attractant by activating the histamine $H_4$ receptor expressed on mast cell surface. The histamine receptor is expressed on the surface of mast cells, and release of histamine from mast cells upon degranulation serves as a mechanism via histamine receptor activation, for mast-cell recruitment into the retina.

Example 5: Small Interfering RNA (siRNA) Molecules can Prevent Secretion of Renin from Mast Cells This Example describes experiments testing whether siRNA molecules can affect secretion in HMC-1 cells.

Renin-specific siRNA duplexes were made based on the coding sequence of human renin between exons 2-8 (Dharmacon) (accession number M26900). The four siRNA duplexes were made against the following renin sequences:

```
32GTACAGCACTTTTCTATTT50;      (SEQ ID NO: 5)

2792TCAACTTGCTGGCCTCTTA2810;  (SEQ ID NO: 6)
```

```
3824GCAAAGAGAGTACATAACA3842;      (SEQ ID NO: 7)
and

5519GAGAAAGGCTGGACAGAGA5537.      (SEQ ID NO: 8)
```

The negative control was a non-specific scrambled siRNA duplex between:

```
5'-AUGUAUUGGCCUGUAUUAGUU-3';      (SEQ ID NO: 9)
and

3'-UUUACAUAACCGGACAUAAUC P-5'.    (SEQ ID NO: 10)
```

To assess the efficacy of this siRNA approach, the activity of renin protein was measured both before siRNA transfecting and at 48 hours after transfection of the HMC-1 cells.

HMC-1 cells were seeded in 6-well plates. Cells were transfected either with: renin siRNA duplexes (50 nM), scrambled siRNA duplex (50 nM), or treated with the transfection reagent (control), and maintained for 48 hours. An aliquot of cells from each well was counted to estimate the cell number before (initial) and 48 hours after transfection (post). The ability of the siRNA duplexes to silence renin mRNA in the transfected HMC-1 cells was determined by comparing the amount of ANG I formed in the releasate pre- and post-transfection by radioimmunoassay (RIA). Releasate was collected twice during the experimental protocol, by exposing each well of HMC-1 cells to the degranulating agent 48/80 (20 µg/ml) either immediately before or 48 hours post-transfection. The amount of ANG I generated on each sample is expressed as pg ANG I formed/ml/hr/$10^5$ cells. The effect of the siRNA on the amount of renin protein produced by the cell was determined by comparing the initial and final amounts of ANG I formed (renin activity) by the releasates.

Figure 12:
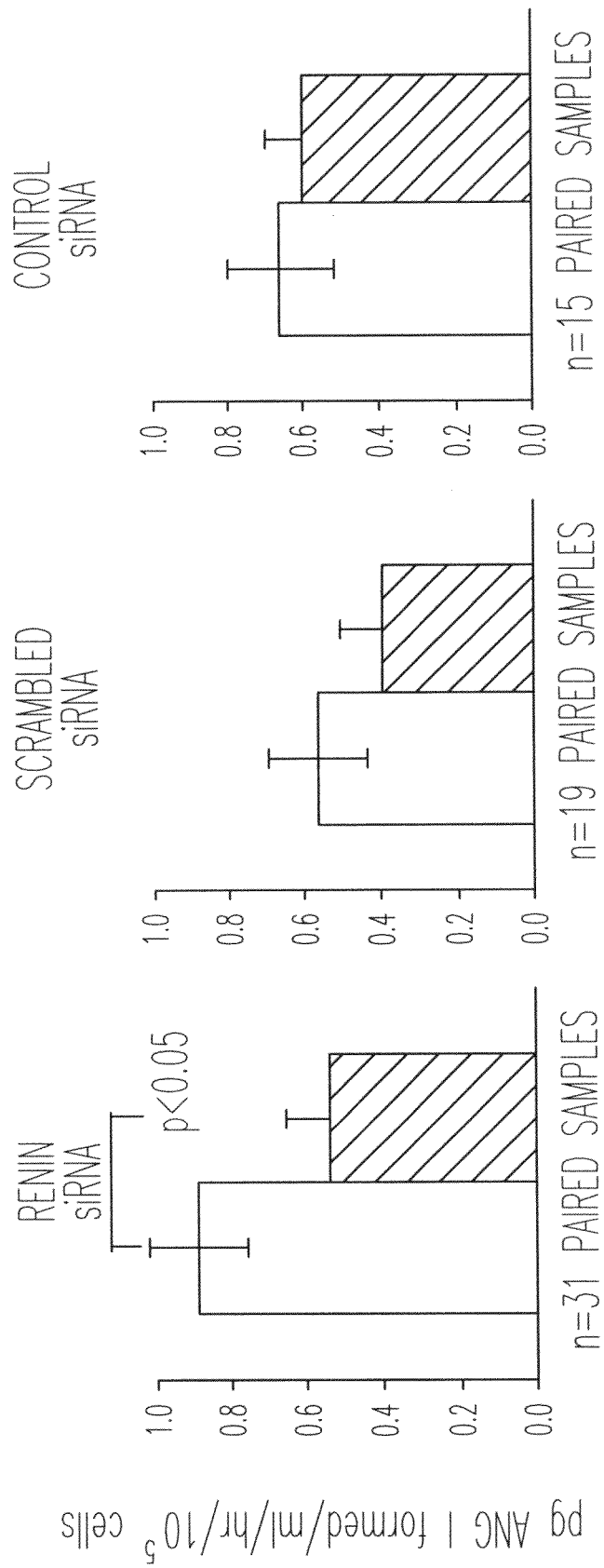
FIG. 12 graphically illustrates the amount of Angiotensin I formed (pg/ml/hr/$10^5$ cells) by HMC-1 cell lysates before (open bars) and 48 hours after transfection (shaded bars) with renin siRNA (50 nM), scrambled siRNA (50 nM), or cells treated with transfection reagent alone (control). As illustrated, the renin siRNA inhibits significantly more renin activity as detected by the amount of Angiotensin I formed.

As shown in FIG. 12, HMC-1 cells transfected with renin siRNA, exhibited an approximate 40% decrease in renin activity as assessed by the absolute amount of ANG I formed compared to the amount measured from these cells before transfection. There was no significant decrease in the amount of ANG I formed in HMC-1 exposed to the scrambled control siRNA (control) or in cells exposed to the transfection reagent (control).

Example 6: Mast Cell Degranulation, Renin Release, Local ANG II Formation, and Vasoconstriction in Diabetes This Example illustrates the effect of a mast-cell derived factor on the kidneys of STZ-induced diabetic rats.

Mast-cell degranulation was induced with agent 48/80, which will release renin, as the inventors have previously shown, as well as numerous other mediators synthesized and stored by mast cells. In order to assess the contribution of renin, and the subsequent angiotensin formed, to the increase in vascular resistance observed with mast cell degranulation, the highly selective renin inhibitor BILA2157 was used.

Figure 17:
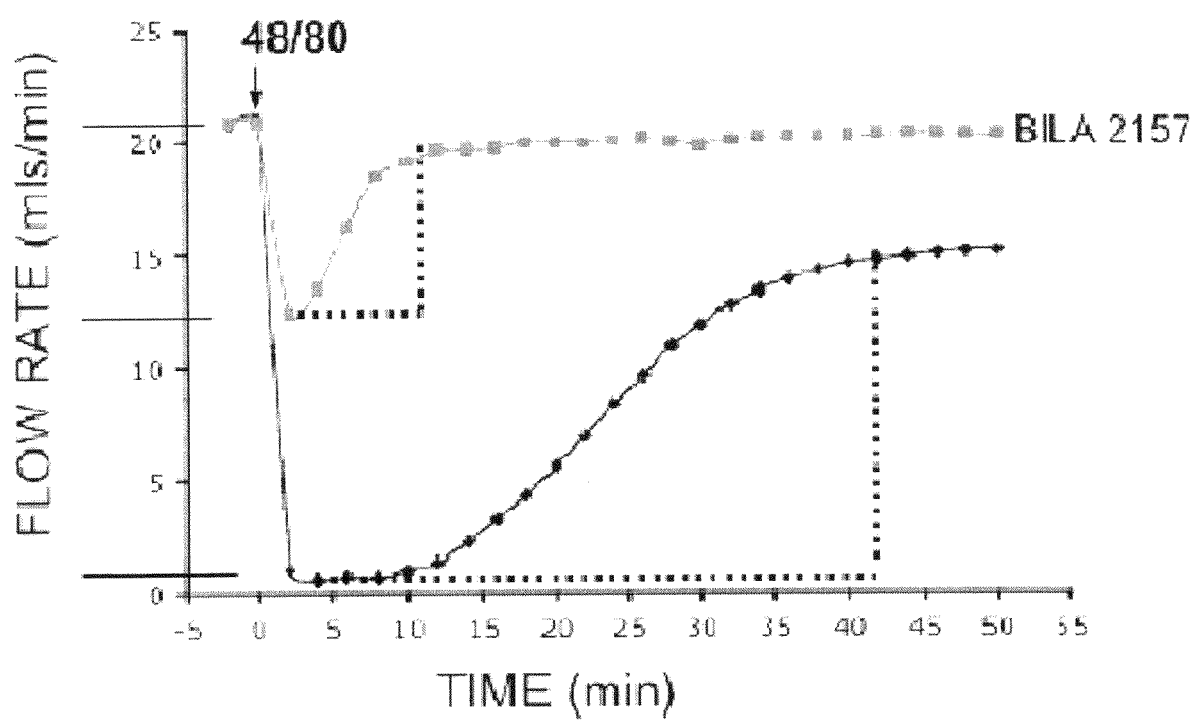
FIG. 17 shows representative traces illustrating the flow rate (ml/min as a function of time (min) in two isolated and perfused 28-day diabetic kidneys where one rat was treated with a mast cell stabilizer, BILA 2157 (■), while the other rat was not treated with the mast cell stabilizer (♦). The mast cell degranulating agent 48/80 (20 µg/ml) was added to the perfusate at the time-point indicated by the arrow. As shown, the mast stabilizer BILA 2157 offsets the rate reducing effects that the mast cell degranulating agent has upon kidneys.

FIG. 17 shows kidney flow rate responses typically observed for isolated perfused diabetic kidneys. Flow rate (ml/min) was measured under constant perfusion pressure, and is plotted against time (min). The upper (■) line in FIG. 17 shows the flow rate of a diabetic rat kidney treated with 100 nM BILA 2157, which was added to the perfusate prior to injection of the 48/80 degranulating agent (−2 minutes). In the absence of a degranulating agent, the BILA2157 renin inhibitor had no effect on flow rate and was maintained in the perfusate for the remainder of the experiment. The bottom curve (♦) shows a typical response of a diabetic kidney, which was not treated with the BILA2157 renin inhibitor.

After establishing a constant flow rate, mast-cell degranulation was induced by injecting the 48/80 degranulating agent (300 µg/ml) into the renal artery (at arrow). In both control and BILA-treated diabetic kidneys, injection of 48/80 led to a rapid decrease in flow rate due to an increase in renal vascular resistance (i.e. vasoconstriction). However, the magnitude of this vasoconstriction response was markedly different between the two kidneys. The BILA2157-treated diabetic kidney displayed much less vasoconstriction than the untreated diabetic kidney—the flow rate decreased from 20 to 12 ml/min in BILA2157-treated diabetic kidneys, whereas the untreated diabetic kidney decreased from a flow rate of 20 to 1 ml/min. Moreover, the return to baseline flow rate was much faster in the BILA2157-treated diabetic kidney (~8 min) compared to the untreated diabetic kidney (~40 min). The rate of the initial flow recovery was also greater in the BILA-treated diabetic kidney (0.5 mls/min/min) compared to the untreated diabetic kidney (0.3 mls/min/min). Moreover, the untreated diabetic kidney did not return to the baseline level after exposure to the 48/80 degranulating agent. In situ, the time it takes to return to normal flow after an acute increase in vascular resistance can profoundly influence the extent of ischemic damage in the kidney.

Example 7: Treatment with Mast Cell Stabilizer Reduces Tortuosity of Vasculature As shown in FIG. 2 increased retinal vascular permeability and neovascularization in proliferative diabetic retinopathy is found at the interface of the retina and vitreous in humans. This Example describes an analysis of the retinal vasculature from fixed eyes of control (A), diabetic (B), and cromolyn-treated diabetic (C) rats.

Figure 13A:
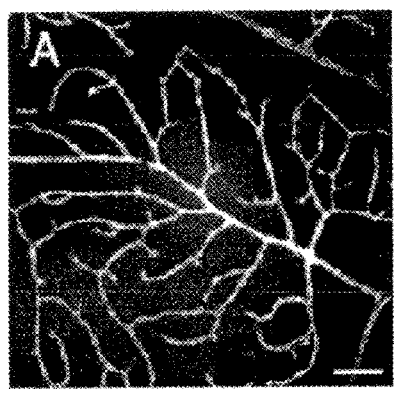
FIG. 13A-C show retinal whole mounts stained with the endothelial cell marker, FITC-Griffonia lectin from a control rat retina (FIG. 13A), a diabetic rat retina (FIG. 13B, and from a cromolyn-treated diabetic rat retina (FIG. 13C). Scale bar, 100 µm.
Figure 13B:
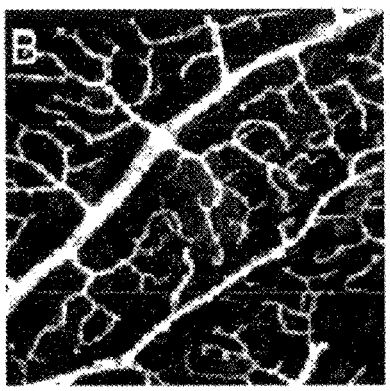
Figure 13C:
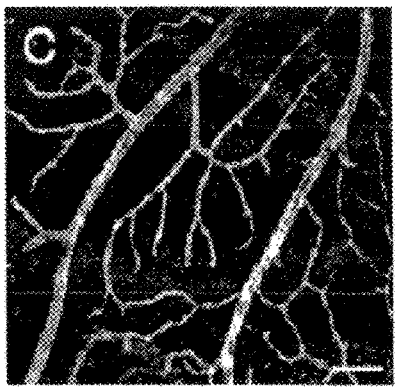

FIG. 13 shows retinal whole mounts that were stained with the endothelial cell marker, griffonia lectin, which was conjugated to FITC to permit visualization of retinal capillaries. As shown in FIG. 13B, diabetes is correlated with tortuosity of the retinal microvasculature. These abnormal changes in the vessel morphology were not observed in the eyes of the cromolyn-treated diabetic rat (FIG. 13C), which exhibited vascular morphology similar to the non-diabetic rat eye (FIG. 13A).

Example 8: Treatment with Mast Cell Stabilizer Reduces Vascular Permeability

This Example shows that a mast cell stabilizer reduced the permeability of retinal vasculature.

The STZ-induced diabetic rat model (Long Evans strain) (40 mg/kg body wt; 28 days) was used for these studies. Fluorescein angiography was performed to assess the permeability of the retinal vasculature in these rats. The pigmented eyes of this strain facilitate angiography. Diabetic rats were treated with the mast cell stabilizer Na-cromolyn and the vascular permeability of these treated rats was compared to diabetic rats that were not treated with Na-cromolyn.

Figure 14:
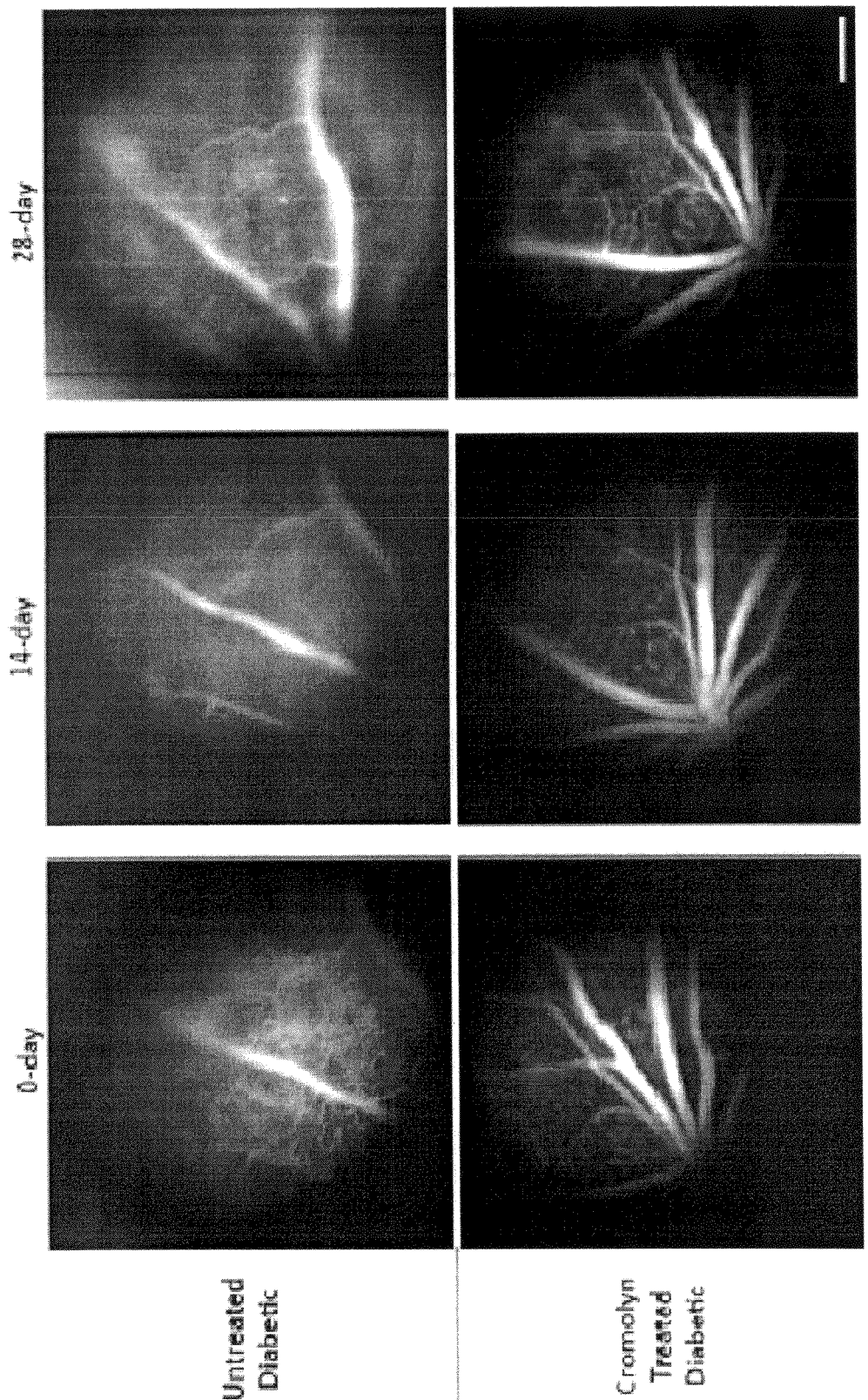
FIG. 14 illustrates that stabilizing mast cells reduces retinal vascular leakiness. Fluorescein angiography of Long-Evans rat eyes at time zero (prior to STZ-injection), at 14-days, and at 28-days after STZ-injection. All angiograms were measured 10-minutes after IP injection of dye. MC stabilization (cromolyn-treated) reduces the leakage of fluorescein from retinal vessels (scale bar=100 µm).

Vascular permeability was determined over time in the untreated and treated hyperglycemic state (FIG. 14). Leakiness was greatly increased in the untreated rats (STZ, n=3 rats vs. con, n=3 rats). The leakiness was greatly diminished in eyes treated with the Na-cromolyn (n=3 rats).

Weekly angiograms were also performed on control rats, STZ-injected, and STZ-injected rats treated with the mast cell stabilizer, Na cromolyn (2%), topically administered to the eyes (2 drops b.i.d.).

FIG. 15 shows the retinal vasculature on day 28 from a non-diabetic control (FIG. 15A), diabetic (FIG. 15B), and cromolyn-treated diabetic (FIG. 15C) rat. Leakage of dye out of the vessels was apparent in the untreated diabetic rat eye (FIG. 15B), as seen by the pooling of dye. However, topical treatment with the mast cell stabilizer prevented dye pooling (FIG. 15C).

These data indicate that mast cells have a role in diabetic retinopathy and that administration of mast cell stabilizer can be used to treat and inhibit the onset and progression of diabetic retinopathy.

Example 9: Mast Cell Stabilization Prevents Vascular Leakiness in the Hyperglycemic Retina This Example further illustrates that stabilizing ocular mast cells prevents retinal capillary leakage in STZ-induced hyperglycemic rats, an animal model of type-1 diabetes.
Materials and Methods The STZ-induced diabetic rat model (Long Evans strain) (40 mg/kg body wt; 28 days) was used for fluorescein angiography experiments. The pigmented eyes of this strain facilitate angiography. To evaluate the role of mast cells, weekly angiograms were performed on control rats, STZ-injected, and STZ-injected rats treated with the mast cell stabilizer, Na cromolyn (4%), topically administered to the eyes (2 drops b.i.d.). Leakage of dye out of the vessels was apparent in the untreated diabetic rat eye as seen by the pooling of dye. Topical treatment with the mast cell stabilizer prevented dye pooling and is consistent with the hypothesis that mast cells are contributing to microvascular leakiness in diabetic retinopathy.

In order to verify this finding, additional experiments were designed to measure leakiness across the blood-retinal barrier of STZ-induced hyperglycemic Long-Evans rats and to determine whether mast cell stabilization reduces vascular permeability in the hyperglycemic state. Blood glucose levels were monitored weekly to verify the hyperglycemic state. The three groups of animals were as follows: untreated hyperglycemic, cromolyn-treated hyperglycemic, and normo-glycemic (vehicle injected). The hyperglycemic group of rats was treated with the mast cell stabilizer (Na cromolyn, 4%) by topical administration to the eyes (2 drops twice a day), as described above.

Technique for Evaluating Vascular Permeability:

Measurements of the Evan's Blue dye concentration across the blood-retinal barrier were performed on day 15 post±STZ-injection. Rats were anesthetized and Evan's Blue dye injected (45 mg/kg) into either lateral vein in the distal segment of the tail. Successful Evan's Blue infusion was confirmed if the animals visually turned blue following dye injection. After two-hours of dye circulation, the animals were re-anesthetized then opened at the chest. Blood was drawn from the left ventricle, and the animals were perfused via the left ventricle for 2 minutes with pH 3.5, 0.05M citrate-buffered, 1% paraformaldehyde solution at 37° C. Both eyes were then enucleated and their retinas were removed and dried overnight (for tissue dry weight). Each retina was then placed in 120 µl formamide overnight at 60° C. to extract the Evan's Blue from the tissue. The formamide was subsequently pipetted from each retina and filtered through 30 Kd MW centrifugal filters (Millipore) at 3000 rpm for 2 hours. 100 µl of the filtrate was then measured in a spectrophotometer at 620 nm, the dye's absorbance maximum. The dye's absorbance minimum, 740 nm, served as a reference wavelength. Dilutions (1:1000 in formamide) of the collected plasma were also measured spectrophotometrically at this time. Sample absorbance measurements were converted to concentrations using absorbance measurements from known concentrations of Evan's Blue in formamide. Dye leakage from blood to retina was calculated as:

$$\frac{[\text{sample dye concentration}] \ (\mu g/\mu l)}{[\text{plasma dye concentration}] \ (\mu g/\mu l) * \text{dry weight retina} \ (\mu g) * \text{dye circ time (hrs)}}$$

Results

Figure 19:
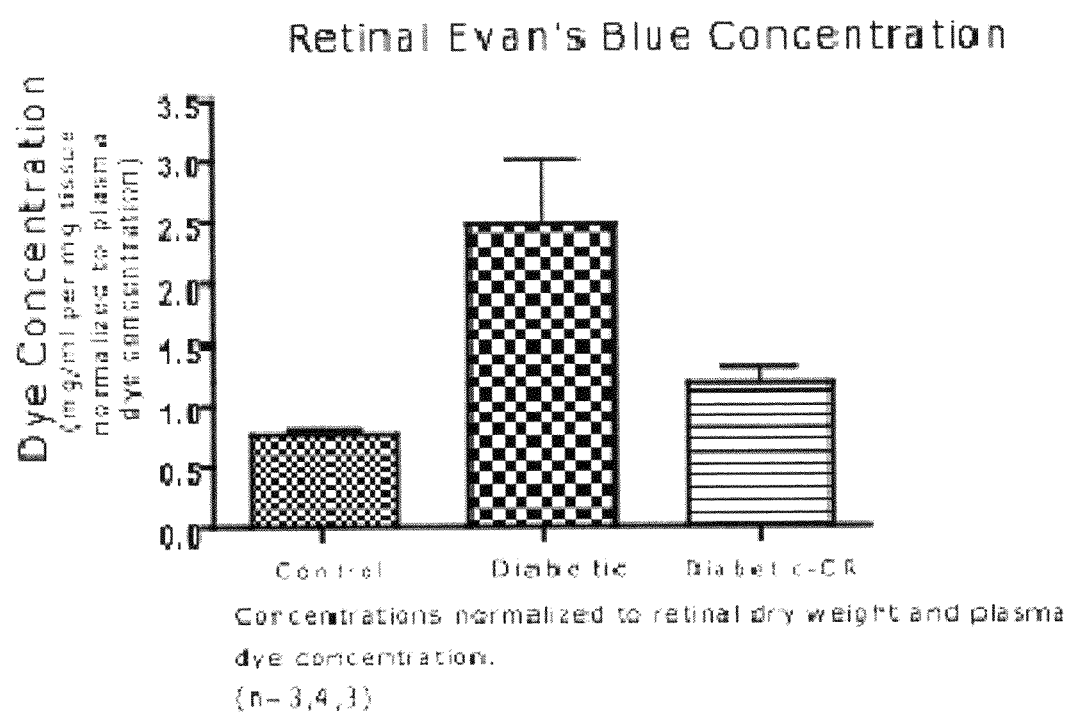
FIG. 19 graphically illustrates Evan's Blue dye concentration in the retina of eyes from diabetic rats (center bar) compared to control, non-diabetic rats (left bar) and mast cell stabilizer-treated diabetic rats (diabetic-CR; right bar). As illustrated, substantially less dye concentration is observed in the retina of eyes from diabetic rats treated with a mast cells stabilizer than in untreated diabetic rat retinas. Dye concentration in the eyes is one measure of vascular leakiness, which is a symptom of diabetic retinopathy.

Treatment with Na-cromolyn prevented dye leakage into the retinal space in hyperglycemic rats, as determined by measuring the distribution of Evan's Blue dye across the blood-retinal barrier. FIG. 19 is a graph illustrating that control eyes from the normo-glycemic rats (Control, n=3 rats) displayed minimal leakiness of the dye across the blood-retinal barrier. This basal leakiness was similar to that observed in the cromolyn treated eyes from hyperglycemic rats (Diabetic-CR, n=4 rats) (p>0.05).

However, there was a significant difference in the level of leakiness across the blood-retinal barrier between eyes from the hyperglycemic (Diabetic, n=3 rats) and the normoglycemic (Control) (p<0.05) rats and between the hyperglycemic (Diabetic) and hyperglycemic cromolyn-treated rats (Diabetic-CR) (p<0.05). Taken together these results show that treatment with mast cell stabilizers such as Na-cromolyn protects against the early phase of increased vascular permeability, a precursor to blindness in the STZ-rat model of type 1 diabetes.

Diabetic retinopathy, a complication of diabetes, is the leading cause of blindness in developed countries. It is the most frequent cause of new cases of blindness among adults aged 20-74 years. During the first twenty years of disease, nearly all patients with type I diabetes and >60% of patients with type 2 diabetes have retinopathy. Diabetic retinopathy progresses from mild non-proliferative abnormalities, exemplified by increased vascular permeability, to moderate and severe non-proliferative diabetic retinopathy characterized by vascular closure.

Therefore, an ophthalmic cromolyn Na solution (4%) that can be prescribed for humans, exhibits a protective effect against increased vascular permeability, an early manifestation of diabetic retinopathy, in a rodent model of type I-diabetes. In particular, the results described herein indicate that treatment with mast cell stabilizers can inhibit the onset and/or progression of diabetic retinopathy.

These latest findings, using the standard method for measuring leakiness of the retinal vasculature, confirm our earlier findings with fluorescein angiography. Together they provide proof that early phase of diabetic retinopathy can be treated with a drug already approved by the FDA. This is a new use (diabetic retinopathy) for Na-cromolyn. Re-formulation of Na-cromolyn with a longer half-life and/or in concert with a delivery system that slowly releases the drug directly in the eyes over the course of a day may obviate the need for topical administration of the drug to the eyes twice a day.

Example 10: Diabetic Retinopathic Lesions from Humans Contain Renin-Positive Mast Cells This Example illustrates that lesions present in human diabetic retinopathy tissues are infiltrated by mast cells that contain renin.

Figure 20:
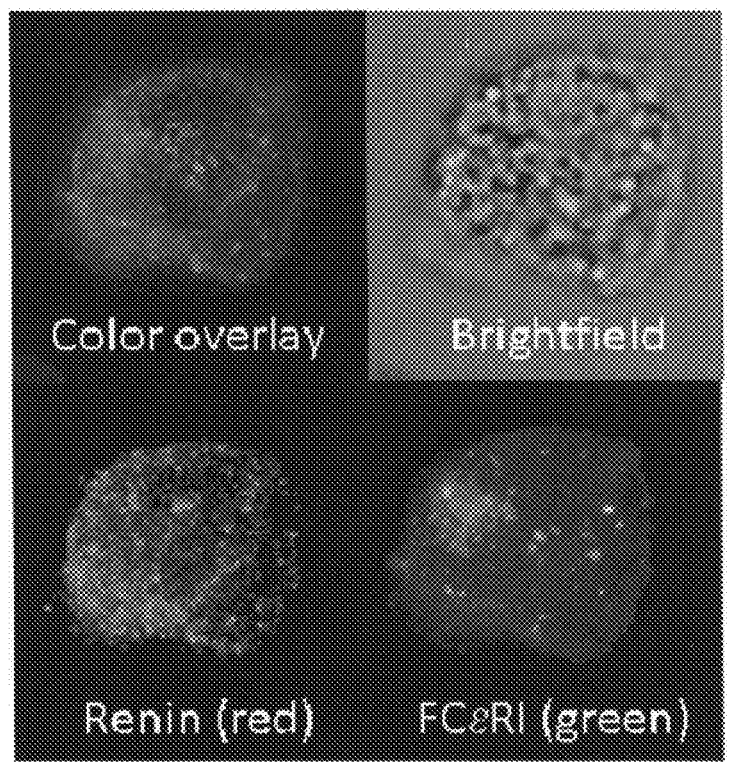
FIG. 20 shows representative cells from human diabetic retinopathy lesions that were stained with antibodies that react specifically with mast cells (anti-FCεRI antibodies, that stain green) and with human renin (anti-renin antibodies that stain red).

Fibrotic tissue from human diabetic retinopathic lesions was obtained and screened for mast cells using an antibody to FCεRI, which is highly selective for a mast cell surface protein. FIG. 20 indicates that mast cells were present in the fibrotic lesion. Furthermore, these mast cells positive stained for renin, as detected using an anti-renin antibody.

Example 11: Mast Cell Stabilizers Reduce VEGF Levels in Diabetic Rat Retinas

This Example illustrates that treatment of STZ-induced hyperglycemic diabetic rats with Na-Cromolyn, a mast cell stabilizer, reduces vascular endothelial growth factor (VEGF) levels in the retinas of these animals.

The STZ-induced diabetic rat model (Long Evans strain) (40 mg/kg body wt; 28 days) was used for these studies. To evaluate the effect of a mast cell stabilizer on VEGF levels, STZ-injected rats were treated with the mast cell stabilizer, Na-Cromolyn (4%), topically administered to the eyes (2 drops b.i.d.). VEGF levels were measured in the retinas of STZ-injected diabetic rats treated with Na-Cromolyn and these levels were compared to VEGF levels in the retinas of control rats and in the retinas of STZ-injected diabetic rats that received no Na-Cromolyn. Control rats received no streptozotocin (STZ) and no Na-Cromolyn.

Figure 21:
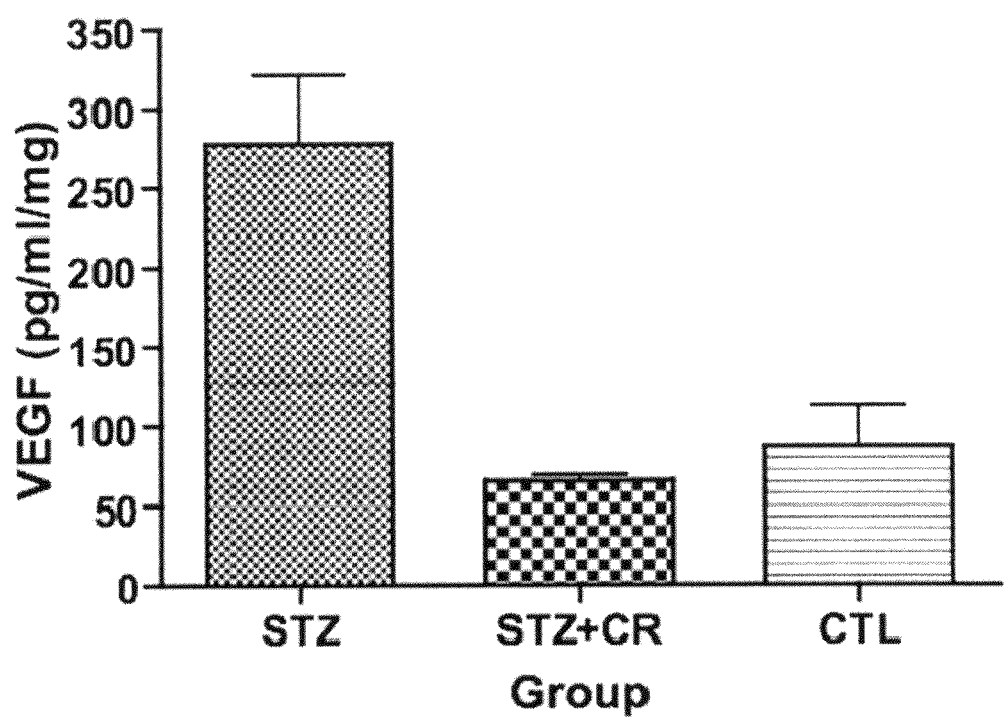
FIG. 21 shows a bar graph illustrating that treatment of diabetic rats with a mast cell stabilizer (Cromolyn Na) decreases vascular endothelial growth factor (VEGF) levels in the retinas of these rats. The bar graph shows the concentration of VEGF, per mg of retina, from 1 month hyperglycemic rats. STZ (diabetic rats; n=4 animals, one retina/animal); STZ+Cromolyn (diabetic rats treated with Cromolyn Na; n=2 animals, one retina/animal); control (non-diabetic rats, not treated with Cromolyn Na; n=3 animals, one retina/animal).

FIG. 21 shows that VEGF levels are elevated to about 275 pg VEGF/ml/mg retina in STZ-injected hyperglycemic rats. However, in STZ-injected hyperglycemic rats that were treated with Na-Cromolyn, VEGF levels were similar to control levels at about 65 pg VEGF/ml/mg retina.

VEGF is a potent angiogenic and vascular permeability factor and is implicated in the onset and progression of diabetic retinopathy. The data presented herein indicate that administration of mast cell stabilizers to the eyes of hyperglycemic and/or diabetic subjects can reduce VEGF levels. Thus, mast cell stabilizers can be used to treat and inhibit the onset of diabetic retinopathy.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A method comprising administering cromolyn twice a day to the mammal's eye in an amount effective to decrease vascular endothelial growth factor (VEGF) in the retinal vasculature within the vitreous cavity of the mammal's eye, where the cromolyn is administered with lodoxamide, nicardipine, barnidipine, elgodipine, a dihydropyridine, or a combination thereof to thereby reduce VEGF in the retinal vasculature of the mammal and treat angiogenesis in the retinal vasculature of the mammal's eye.

2. The method of claim 1, wherein a therapeutically effective amount of the cromolyn is topically administered to the eye.

3. The method of claim 1, wherein the cromolyn is administered at dosages lower than systemic dosages of cromolyn for the mammal.

4. The method of claim 3, wherein the therapeutically effective amount of the cromolyn is about 0.01 to about 2 g.

5. The method of claim 1, wherein the cromolyn, lodoxamide, nicardipine, barnidipine, elgodipine, a dihydropyridine, or a combination thereof, are administered in an implant device.

6. The method of claim 1, wherein mast cells are present in an ocular space of the mammal's eye.

* * * * *

SEQUENCE LISTING

<160> NUMBER OF SEQ ID NOS: 10

<210> SEQ ID NO 1
<211> LENGTH: 19
<212> TYPE: DNA
<213> ORGANISM: Homo sapiens

<400> SEQUENCE: 1
gagaaaggct ggacagaga                                        19

```
<210> SEQ ID NO 2
<211> LENGTH: 19
<212> TYPE: DNA
<213> ORGANISM: Homo sapiens

<400> SEQUENCE: 2
tcaactggct ggcctctta                                                  19

<210> SEQ ID NO 3
<211> LENGTH: 19
<212> TYPE: DNA
<213> ORGANISM: Homo sapiens

<400> SEQUENCE: 3
gtacagcact tttctattt                                                  19

<210> SEQ ID NO 4
<211> LENGTH: 19
<212> TYPE: DNA
<213> ORGANISM: Homo sapiens

<400> SEQUENCE: 4
gcaaagagag tacataaca                                                  19

<210> SEQ ID NO 5
<211> LENGTH: 19
<212> TYPE: DNA
<213> ORGANISM: Homo sapiens

<400> SEQUENCE: 5
gtacagcact tttctattt                                                  19

<210> SEQ ID NO 6
<211> LENGTH: 19
<212> TYPE: DNA
<213> ORGANISM: Homo sapiens

<400> SEQUENCE: 6
tcaacttgct ggcctctta                                                  19

<210> SEQ ID NO 7
<211> LENGTH: 19
<212> TYPE: DNA
<213> ORGANISM: Homo sapiens

<400> SEQUENCE: 7
gcaaagagag tacataaca                                                  19

<210> SEQ ID NO 8
<211> LENGTH: 19
<212> TYPE: DNA
<213> ORGANISM: Homo sapiens

<400> SEQUENCE: 8
gagaaaggct ggacagaga                                                  19

<210> SEQ ID NO 9
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 9
```

```
auguauuggc cuguauuagu u                                    21

<210> SEQ ID NO 10
<211> LENGTH: 21
<212> TYPE: RNA
<213> ORGANISM: Artificial Sequence
<220> FEATURE:
<223> OTHER INFORMATION: A synthetic siRNA

<400> SEQUENCE: 10
cuaauacagg ccaauacauu u                                    21
```